(12) United States Patent
Sambandan

(10) Patent No.: US 9,933,382 B2
(45) Date of Patent: *Apr. 3, 2018

(54) GAS SENSOR ELEMENT

(71) Applicant: NITTO DENKO CORPORATION, Osaka (JP)

(72) Inventor: Ekambaram Sambandan, Carlsbad, CA (US)

(73) Assignee: NITTO DENKO CORPORATION, Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/621,949

(22) Filed: Jun. 13, 2017

(65) Prior Publication Data
US 2017/0276628 A1 Sep. 28, 2017

Related U.S. Application Data

(63) Continuation of application No. 14/723,379, filed on May 27, 2015, now Pat. No. 9,739,738.

(60) Provisional application No. 62/107,961, filed on Jan. 26, 2015, provisional application No. 62/003,753, filed on May 28, 2014.

(51) Int. Cl.
*G01N 33/497* (2006.01)
*G01N 27/12* (2006.01)
*G01N 33/00* (2006.01)
*H01L 29/04* (2006.01)
*H01L 29/24* (2006.01)
*G01N 1/22* (2006.01)

(52) U.S. Cl.
CPC ....... *G01N 27/125* (2013.01); *G01N 33/0047* (2013.01); *G01N 33/497* (2013.01); *H01L 29/04* (2013.01); *H01L 29/24* (2013.01); *G01N 2001/2244* (2013.01); *G01N 2800/042* (2013.01)

(58) Field of Classification Search
CPC ............. G01N 27/125; G01N 33/0047; G01N 33/497; G01N 2001/2244; G01N 2033/4975
See application file for complete search history.

(56) References Cited

U.S. PATENT DOCUMENTS

2005/0109617 A1* 5/2005 Ono .................. B22F 3/114
204/400
2009/0148347 A1* 6/2009 Lee .................. C04B 35/4682
422/83

OTHER PUBLICATIONS

Wang et al., "Ferroelectric WO3 Nanoparticles for Acetone Selective Detection", Chem. Mater. 2008, vol. 20, pp. 4794-4796.*
Kanan et al., "Semiconducting Metal Oxide Based Sensors ofr Selective Gas Pollutant Detection", Sensors 2009, vol. 9, pp. 8158-8196.*
Ferroni, "Nanosized thin films of tungsten-titanium mixed oxides as gas sensors", Sensors and Actuators B, 1999, vol. 58, pp. 289-294.*

* cited by examiner

*Primary Examiner* — Justin Olamit
(74) *Attorney, Agent, or Firm* — K&L Gates LLP; Louis C. Cullman; Robert W. Winn

(57) ABSTRACT

Described herein are sensor elements for detecting the presence of organic materials comprising a boron doped n-type semiconductor material with decrease in resistivity upon organic materials exposure with increase in resistivity upon organic materials exposure.

15 Claims, 9 Drawing Sheets

GAS SENSOR ELEMENT

CROSS REFERENCE TO RELATED APPLICATIONS

This application is a continuation of U.S. patent application Ser. No. 14/723,379, filed on May 27, 2015, which claims the benefit of U.S. provisional patent application Nos. 62/003,753 and 62/107,961, filed May 28, 2014 and Jan. 26, 2015, respectively. The disclosures of all of these applications are incorporated by reference herein in their entireties.

BACKGROUND

Field

Some embodiments are related to medical devices, and also related to oxide compositions for qualitative or quantitative analysis of breath components.

Description of the Related Art

Scientists have discovered connections between certain illnesses and physical conditions that are associated with the presence of certain gases in mammalian expiratory breaths. To that end, gas sensing devices have been reported. However, some acetone sensing devices require higher than ambient operating temperatures, in some cases in excess of 300° C. Heating may provide energy to the semiconductor material and increase the movement of electrons across the band gap. However, such high operating temperatures can contribute to difficulties in creating portable devices.

Thus there is a need for an acetone sensor that operates at room temperatures for use in portable devices that could be used for diagnosis and self-monitoring of outpatients having various physical conditions, including diabetes.

SUMMARY

This application is related to an acetone sensor element that detects the presence of acetone in a gas sample, e.g., exhaled air. Some embodiments relate to an gas sensor element, such as an acetone sensor element or an ethanol sensor element, that works at ambient temperatures.

Some embodiments include a gas sensor element comprising: a first electrode and second electrode, wherein the first electrode and the second electrode are separated by a gap of about 1 to about 10 mils; and a polycrystalline n-type semiconductor material wherein the semiconductor material physically contacts both the first and second electrodes.

Some embodiments include a method for determining acetone in a subject's breath comprising exposing a mammalian breath sample to a gas sensor comprising a gas sensor element of claim 1, wherein the presence of acetone is detected by a change in resistivity across the sensor.

Some embodiments include a semiconductor composite having a sensor element that comprises:

$$P_{1-x}B, \quad \text{(Formula 1)}$$

wherein P is an n-type semiconductor material, B is boron and x is 0.10. In some embodiments, x is >0.0001. In some embodiments, the n-type semiconductor material can be tungsten oxide ($WO_3$). In some embodiments, the $WO_3$ is epsilon phase $WO_3$ ($\epsilon$-$WO_3$). In some embodiments, the sensor element can further comprise a co-catalyst. In some embodiments, the co-catalyst can be a noble metal. In some embodiments, the noble metal is palladium, gold or platinum. In some embodiments, the co-catalyst can be a transition metal oxide. In some embodiments, the transition metal oxides can be an oxide of Co, Mn, Ni, or Cu.

In some embodiments, a gas sensor element is provided. The sensor element can comprise a physical mixture of $WO_3$ and $CeO_2$. In some embodiments, the physical mixture comprises a 1:1 mole ratio. In some embodiments, the $WO_3$ is gamma phase $WO_3$. In some embodiments, the $WO_3$ is epsilon phase. In some embodiments, the sensor element can further comprise co-catalyst. In some embodiments, the co-catalyst can be selected from the metal oxides. In some embodiments, the metal oxide is $CeO_2$ or $TiO_2$.

In some embodiments, a method for making sensor composition is described, the method comprising creating a n-type semiconductor precursor aqueous solution; heating the solution in a preheated appliance, wherein the preheated appliance has been preheated to substantially near the combustion temperature of the aqueous solution; combustion-reacting the precursor solution; and annealing the combustion reaction product. In some embodiments, the appliance can be preheated to at least about 420° C.

In some embodiments, a method is described, the method comprising combustion synthesizing a boron doped epsilon or gamma phase $WO_3$ semiconductor; providing an interdigitated sensor element having a first and second spaced apart electrodes; and disposing the combustion-synthesized boron doped epsilon or gamma phase semiconductor between a first and second separated electrodes. In some embodiments the method further comprises increasing the synthesized boron doped epsilon or gamma phase semiconductor specific surface area (SSA) to greater than 10 $m^2/g$, ball milling the boron doped epsilon or gamma phase $WO_3$ semiconductor between about 5 to about 48 hours. In some embodiments, increasing the SSA of the boron doped epsilon or gamma phase $WO_3$ semiconductor comprises ball milling the boron doped epsilon or gamma phase $WO_3$ semiconductor between about 5 to about 25 hours. In some embodiments, increasing the SSA comprises sonicating the boron doped epsilon or gamma phase $WO_3$ semiconductor before disposition between the first and second electrode. In some embodiments, the method can further comprise adding a metal oxide to the boron doped epsilon or gamma phase $WO_3$ semiconductor These and other embodiments are described in greater detail below.

BRIEF DESCRIPTION OF THE DRAWINGS

FIG. 7A is a depiction of an embodiment of a device described herein.

DETAILED DESCRIPTION

Figure 1:
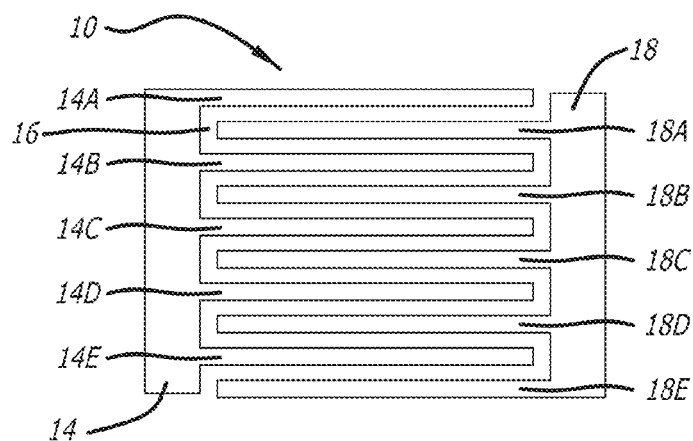
FIG. 1 is a plan view of some embodiments of a device described herein.

The term "polycrystalline material" includes any material comprising a plurality of grains (i.e., crystals) of the material that are bonded directly together by inter-granular bonds. The crystal structures of the individual grains of the material may be randomly oriented in space within the polycrystalline material.

As used herein, the term "inter-granular bond" includes any direct atomic bond (e.g., covalent, metallic, etc.) between atoms in adjacent grains of material.

As used herein, the term "epsilon phase" has the ordinary meaning known to a person of ordinary skill in the art.

As used herein, the term "gamma phase" has the ordinary meaning known to a person of ordinary skill in the art.

As used herein, the term "doped" includes elements that are incorporated into the crystal lattice of the compound, for example as substituted within defined positions within the crystal lattice or otherwise interstitially included within the crystal.

The term "loaded" includes the non-valent combination, e.g., a physical mixture and/or adjacent disposition of a first material, e.g., the n-type semiconductor material, and a second material, e.g., with noble metals at the surface such as Pt, Ag, Pd, Au.

The term "n-type semiconductor" has the ordinary meaning known to a person of ordinary skill in the art.

The term "room temperature" has the ordinary meaning known to a person of ordinary skill in the art.

Some embodiments include a compound represented by Formula 1:

$$P_{1-x}B \quad \text{(Formula 1)},$$

wherein, with respect to Formula 1, P can be an n-type semiconductor material, B can be boron and x is ≤0.10. In some embodiments, the x can be between a lower limit of 0.0001, 0.01, 0.05, 0.10 wt % ratio to an upper limit of about 0.4, 0.5%, 0.75, 1.0 wt % and/or any combination of the described limits. In some embodiments, the x can be 0.225 g (B)/100 g (semiconductor).

Tungsten oxide is one material used in gas sensors. Tungsten Oxide ($WO_3$) crystals can be formed by corner and edge sharing of $WO_6$ octahedra. Various phases can be obtained by corner sharing, e.g., monoclinic II (epsilon [ε]-phase); triclinic (delta [δ]-phase), monoclinic I (gamma [γ]-phase), orthorhombic (beta [β]-phase), tetragonal (alpha [α]-phase), and cubic $WO_3$. The monoclinic II phase may be stable only at subzero temperatures, and monoclinic I may be the most stable phase at room temperature. ε-phase tungsten oxide may be as useful for gas sensors.

In some embodiments, the n-type semiconductor material can be polycrystalline. In some embodiments, the n-type semiconductor material can be $WO_3$. In some embodiments, the n-type semiconductor has an absorption edge of at least 600 nm, at least 550 nm, at least 500 nm, at least 475 nm, and/or at least 450 nm. In some embodiments, the n-type semiconductor material can have an octahedral lattice. In some embodiments, the n-type semiconductor material can be a monoclinic phase material. In some embodiments, the n-type semiconductor material can be a monoclinic I phase material. In some embodiments, the n-type semiconductor material can be a monoclinic II phase material. In some embodiments, the n-type semiconductor material can have a spontaneous dipole moment. In some embodiments, the $WO_3$ can be epsilon phase $WO_3$ ($\epsilon$-$WO_3$). In some embodiments, the $WO_3$ can be gamma phase $WO_3$ ($\gamma$-$WO_3$). In some embodiments, the n-type semiconductor can be epsilon phase tungsten oxide, gamma phase tungsten oxide, and/or mixtures thereof. Comparison of an x-ray diffraction pattern of a given standard and the produced sample is one of a number of methods that may be used to determine whether the sample comprises a particular phase. Exemplary standards include those XRD spectra provided by the National Institute of Standards and Technology (NIST) (Gaithersburg, Md., USA) and/or the International Centre for Diffraction Data (ICDD, formerly the Joint Committee on Powder Diffraction Standards [JCPDS]) (Newtown Square, Pa., USA).

In some embodiments, the semiconductor can comprise at least $\epsilon$-$WO_3$ and at least a second n-type semiconductor material. In some embodiments, the $\epsilon$-$WO_3$ comprises at least 55%, at least 60%, at least 65%, at least 70%, 90%, 95%, or 99% of the n-type semiconductor material. In some embodiments, the % of a $\epsilon$-$WO_3$ is weight %. In some embodiments, the % of a $\epsilon$-$WO_3$ is molar %. In some embodiments, the ratio of $\epsilon$-phase $WO_3$ to γ-phase, can be expressed as the $\epsilon$-phase $WO_3$ XRD peak at about 49.34 2 theta to the γ-phase $WO_3$ XRD peak at about 26.44 2 theta. While not wanting to be bound by theory, it is believed that the spontaneous dipole of the e-$WO_3$ may be related to the material lattice so that changes in the lattice may change the strength of the dipoles (in other words, a change in the spontaneous polarization). It is believed that a change in the spontaneous dipole moment can result in a change in the surface charge of the material.

$WO_3$ compounds, e.g., nanopowders, can be prepared by many different methods including thermal plasma (direct current and including radio frequency inductively-coupled plasma (RF-ICP)), solvothermal, solid state reaction, pyrolysis (spray and flame), and combustion. In some embodiments, the $WO_3$ compounds can be combustion synthesized. Combustion synthesis methods as described in PCT application PCT/US2013/10201, filed Jan. 4, 2014, which is incorporated herein its entirety by reference, are useful because the high temperature may aid in doping boron into the $WO_3$ lattice and/or may contribute to the stabilization of the $\epsilon$-phase $WO_3$. Hence, combustion doping processes may be preferred. For example, when preparing $WO_3$ nanopowders, a liquid dispersion of additional additives, e.g., ammonium metatungstate, ammonium nitrate and/or glycine, in water (5-20 wt % solid in water) can be sprayed into the plasma volume using a two-fluid atomizer. Preferably, the precursor can be present to about 20 wt % solid in water. The plasma can be operated at about 25 kW plate power with, for example, argon, nitrogen and/or oxygen gases. The particles formed from the condensed vapor from the plasma can then be collected on filters. In some embodiments, the particle surface areas range as measured using BET from about 1 m$^2$/g to about 500 m$^2$/g, about 15 m$^2$/g to 30 m$^2$/g, or about 20 m$^2$/g. In some embodiments, the obtained WO$_3$ may be heated from about 200° C. to about 700° C. or about 300° C. to about 500° C.

In some embodiments, the dipole moment of the n-type semiconductor can be modified by changing the semiconductor crystal lattice. In some embodiments the crystal lattice is modified by doping the semiconductor. In some embodiments, the n-type semiconductor can be doped with at least one naturally occurring element, e.g., a group III acceptor element like B on-noble gas elements. In some embodiments the Group III acceptor element can be B. In some embodiments, the dopant can be B. In some embodiments, the dopant can be B$^{3+}$.

In some embodiments, a polycrystalline n-type semiconductor material comprises an epsilon phase WO$_3$ doped with boron, such as B, B$^+$, B$^{2+}$, or B$^{3+}$.

As described above, in some embodiments, the dopant concentration, e.g. B, B$^+$, B$^{2+}$, or B$^{3+}$, can be between a lower limit of about 0.0001%, about 0.01%, about 0.01%, 0.05%, 0.08%, or 0.10%, by weight ratio to an upper limit of about 0.15%, about 0.2%, about 0.4%, about 0.5%, about 0.75%, about 1%, about 2%, or about 5% by weight of the n-type semiconductor, and/or any combination of the described limits. In some embodiments, the X can be about 0.225 g (B)/100 g (semiconductor). While not wanting to be limited by theory, it is believed that if x and/or the dopant concentration is above a threshold amount, the amount of epsilon phase WO$_3$ and/or boron present can be insufficient to provide the desired room temperature phase stability. In addition, while not wanting to be limited by theory, it is believed that if x and/or the dopant concentration is below a threshold amount, the amount of ε-WO$_3$ and/or boron present can also be insufficient to provide the desired room temperature phase stability. While not wanting to be limited by theory, it is believed that if x and/or the dopant concentration is below a threshold amount, the dopant can segregate out instead of doping into the lattice.

Doped elements can be provided as precursors added generally during synthesis. In some embodiments, the dopant can have an ionic diameter of sufficiently small size to increase the stability of the ε-phase WO$_3$. In some embodiments, the dopant can have an ionic diameter of less than about 50 pm (1×10$^{-12}$ meters). In some embodiments, the dopant can have an ionic diameter from about 5 pm, 10 pm, 15 pm, 20 pm, 30 pm, 35 pm, to about 45 pm, to about 50 pm, to about 55 pm. Exemplary ionic diameters for ionic species generally at 90% semiconductor and 10% dopant entities are described in Table 1:

TABLE 1

| Ionic species | Ionic diameter |
|---|---|
| W$^{6+}$ | 74 pm |
| Cr$^{6+}$ | 58 pm |
| Si$^{4+}$ | 54 pm |
| B$^{3+}$ | 41 pm |

The ionic diameter of the desired ionic species can be determined according to Formula 2:

([% molar amount of semiconductor×semiconductor ionic size]+molar amount of dopant×dopant ionic size)/[90%+10%]100     (Formula 2).

For example, for determining B ionic size 90×[W$^{6+}$ ionic size][6660]+0.10×[[580]/100, resulting in a calculated B$^{3+}$ ionic size of about 41 pm. In some embodiments, the dopant can be boron. In some embodiments, the dopant can be B$^{3+}$, e.g., having an ionic diameter of about 41 pm. While not wanting to be bound by theory, it is believed that doping with a smaller ionic diameter dopant molecule than ε-phase WO$_3$, e.g., about 74 pm, can contract the overall cell volume of the crystal, contributing to the stability of ε-WO$_3$ at room temperature.

In some embodiments, the n-type semiconductor can be loaded with at least one metal. Loaded elements can be provided by post synthesis methodologies like impregnation (Liu, M. et al., Chemistry of Materials, published online 2011), photoreduction (Abe et al., Journal of the American Chemical Society, 130:7780-7781, 2008), and sputtering. In some embodiments, the loading may be carried out by electrostatic adsorption. As a preferred embodiment, loading metals on semiconductors may be carried out as described in US Patent Publication Number US2008/0241542 which is incorporated by reference herein in its entirety.

In some embodiments, the loaded element is a noble element. In some embodiments, the loaded element can be a noble element, a noble element oxide, a noble element peroxide (Ag$_2$O$_2$), and/or a noble element hydroxide. In some embodiments, a noble element(s) can be Au, Ag, Pt, Pd, Ir, Ru, Rh, or their oxides and/or hydroxides. In some embodiments, the loaded element is selected from transition metals, their oxides and/or hydroxides. In some embodiments, the loaded element can be Pt or its oxide and hydroxides. In some embodiments, the loaded elements may be chosen from different groups of elements including at least one transition metal and at least one noble metal or their respective oxides and hydroxides A co-catalyst includes a material that enhances the sensor sensitivity. In some embodiments, a co-catalyst may improve sensor sensitivity. For example a co-catalyst may increase the sensitivity by at least about 1.2, at least about 1.5, at least about 1.8, at least about 2, at least about 3, or at least about 5. One method of quantifying rate of sensitivity may include comparing the ascertained sensitivity value of the sensor comprising the co-catalyst to that of a sensor not comprising the co-catalyst. For example, a suitable method of determining the sensitivity value is by the formula: $R_{air}/R_{gas}$ or $R_{gas}/R_{air}$, where $R_{air}$ is the measured resistivity of air (ohms) and $R_{gas}$ is the measured resistivity of the analyte gas, e.g., acetone. See Table 2:

TABLE 2

| Semiconductor | Analyte Gas (Acetone) Concentration | Temperature Of Operation | R Air/R Gas |
|---|---|---|---|
| gamma WO$_3$ | 1 ppm | 300° C. | 1 |
| epsilon WO$_3$:B | 1 ppm | 300° C. | 1.9 |
| 1% PT-E-WO$_3$:B | 1 ppm | 300° C. | 2.77 |
| 1% PT-G-WO$_3$ | 1 ppm | 300° C. | 2.15 |
| gamma WO$_3$ | 100 ppm | room temperature | 1 |
| gamma WO$_3$ + CEO$_2$ | 100 ppm | room temperature | 0.14 |

For example, the presence of a co-catalyst may increase the sensitivity of the sensor about 80% more than its original sensitivity. In some embodiments, the increase in sensitivity is greater than about 10%, about 17.5%, about 25% of its original sensitivity, e.g., about 35-50% and/or about 50 to about 90%, e.g., about 80%.

Some co-catalyst may be compounds or semiconductors that are capable of being reduced by electron transfer from the conduction band of the semiconductor. For example, a co-catalyst may have a conduction band having a lower energy than the conduction band of the semiconductor, or a co-catalyst may have a lowest unoccupied molecular orbital having a lower energy than the conduction band of the semiconductor. An electron loses energy when it is transferred to a band or molecular orbital of "lower energy." An electron gains energy when it is transferred to a band or molecular orbital of "higher energy."

Not wanting to be limited by theory, the inventor believes that some co-catalysts may be metal oxides that are capable of reducing $O_2$. For example, $CeO_2$ can reduce $O_2$ gas by electron transfer. In doing so, it is believed that $Ce^{3+}$ transfers an electron to $O_2$ and is converted to $Ce^{4+}$ as a result. In a semiconductor composition, a semiconductor may transfer an electron to $CeO_2$, thus converting $Ce^{4+}$ to $Ce^{3+}$, and the $Ce^{3+}$ may then reduce $O_2$. $Ce^{3+}$ may also be present as a result of equilibrium processes involving $CeO_2$ and $O_2$, and superoxide radical ion $O_2^-$. $O_2$ and superoxide radical ion in such an equilibrium process may be adsorbed to the surface of solid $CeO_2$ or present in the atmosphere. $Ce^{3+}$ may also be present as a result of oxidation and reduction reactions with cerium species of different oxidation states that may be added intentionally or present as impurities.

Some co-catalysts may be capable of converting atmospheric $O_2$ to superoxide radical ion. For example, $CeO_2$ is capable of converting atmospheric oxygen to superoxide radical ion. It is believed that some of the equilibrium and/or electron transfer processes described above may contribute to this property of $CeO_2$. Such a conversion may occur under a variety of conditions, such as ambient conditions, including for example, normal atmospheric oxygen concentrations, such as about molar concentrations of 10% to about 30%, about 15% to about 25%, or about 20% oxygen; ambient temperature, such as about 0° C. to about 1000° C., about 0° C. to about 100° C., about 10° C. to about 50° C., or about 20° C. to about 30° C.; and pressure, such as about 0.5 to about 2 atm, about 0.8 atm to about 1.2 atm, or about 1 atm. Such a conversion may also occur under elevated or reduced temperature, pressure, or oxygen concentration.

Some co-catalysts may have a valence band or a highest occupied molecular orbital at a higher energy than a valence band of the semiconductor. This may allow a hole in a valence band of the semiconductor to be transferred to a highest occupied molecular orbital or a valence band of the co-catalyst. The hole in the valence band or highest occupied molecular orbital of co-catalyst may then oxidize $H_2O$ or $OH^-$ to $OH$. For example, if $WO_3$ is chosen as a semiconductor, examples of such a co-catalyst may include anatase $TiO_2$, $SrTiO_3$, $KTaO_3$, $SiC$ and/or $KNbO_3$.

In some embodiments, the co-catalyst can be inorganic. In some embodiments, the inorganic co-catalyst can be a binder. In some embodiments, the co-catalyst can be an oxide, such as a metal dioxide, including $CeO_2$, $TiO_2$, or the like. In some embodiments, the co-catalyst can be $SiO_2$, $SnO_2$, $Al_2O_3$, $ZrO_2$, $Fe_2O_3$, $Fe_3O_4$, $NiO$, $Nb_2O_5$, and/or $CeO_2$. In some embodiments, the composite material can comprise a physical mixture of an inorganic co-catalyst and a semiconductor material. In another embodiment, the ratio of the semiconductor material to co-catalyst, e.g., $CeO_2$, may be about 2:3 to about 3:2, such as between 40-60 molar % semiconductor material and 60-40 molar % inorganic co-catalyst, e.g., $CeO_2$. In another embodiment, the ratio of semiconductor material to co-catalyst material, e.g., $CeO_2$, can be about 1:1 [50 molar % to 50 molar %]. In some embodiments, the $CeO_2$ is a sol. In some embodiments, the gas sensor element contains a physical mixture of an n-type semiconductor, such as gamma phase $WO_3$, and a p-type semiconductor, such as $CeO2$. In some embodiments, the gas sensor element contains a physical mixture of gamma phase $WO_3$ and $CeO_2$ in a weight ratio ($WO_3$:$CeO_2$) of about 10:1 to about 1:2, about 5:1 to about 1:1, about 7:3 to about 1:1, or about 13:8.

In some embodiments, the n-type semiconductor, the $WO_3$ compound, doped or undoped, and/or the co-catalyst, or composites thereof, can be combustion synthesized. In some embodiments, the synthesized photocatalytic material can have a specific surface area of greater than about 9 $m^2/g$, 10 $m^2/g$, 12 $m^2/g$, 15 $m^2/g$, 17.5 $m^2/g$, and/or 22 $m^2/g$. The value obtained for specific surface area can be obtained by methods known to those skilled in the art, including, but not limited to, the Brunauer-Emmett-Teller (N2-BET) adsorption method. It was discerned that, when material was combustion synthesized, there was resultant material with an elongated morphogy, e.g., about 50-200 µm in length and about 20 µm in diameter, having a specific surface area of about 6-8 $m^2/g$ (see Example 10, Table 5, see FIG. 12A), e.g., had a SSA of about 7 $m^2/g$ by BET. In some embodiments, while not wanting to be limited by theory, it was discerned that increasing the specific surface area of the combustion synthesized n-type semiconductor, e.g., the compounds of Formula 1, corresponded with an increase in sensor sensitivity.

In some embodiments, increasing the SSA can result from reducing the size of the combustion synthesized particles. In some embodiments, increasing the SSA can result from modifying the elongated rods into more spherical particles of the combustion synthesized particles. In some embodiments, altering the morphology of the combustion synthesized particles can be by making the particles more spherical. In some embodiments, increasing the SSA can be by ball milling the combustion synthesized material. In some embodiments, increasing the SSA can be by sonicating a dispersion of the combustion synthesized material and then selectively removing the reduced size sonicated material.

In some embodiments, increasing the SSA can be by ball milling the combustion synthesized material. In some embodiments, increasing the SSA can result from wet milling the combustion synthesized material. In some embodiments, wet milling can comprise dispersing the desired materials/precursor within a carrier solvent. In some embodiments, the carrier solvent can be a $C_1$-$C_5$ alcohol. In some embodiments, the $C_1$-$C_5$ alcohol can be isopropanol, methanol, and/or ethanol or mixtures thereof. The amount of sample being ball milled, the size of the milling balls, the length of milling time and the speed/rotation of the ball miller instruments are considerations in the amount of ball milling that is sufficient to increase the SSA a sufficient amount. In some embodiments, the milling balls can be about 1 mm to about 10 mm in diameter, e.g., 3 mm and/or 5 mm in diameter. In some embodiments, the milling balls can comprise at least a first and second size plurality of milling balls, the first and second milling balls of different diameters. In some embodiments, the ratio of the first and second milling balls can range from about 1:1 wt % ratio, 2.5:1 ratio, 4:1 ratio, 5:1 ratio, 7.5:1 ratio, and/or a 10:1 wt % ratio, of amount of first milling ball diameter milling balls to amount of second milling ball diameter milling balls. In some embodiments, the first milling balls have a smaller diameter than the second milling balls. For example, for ball milling about 2.00 g $WO_3$/0.05% B and 15.00 ml of methanol, 20 g of 3 mm milling balls and 4 g of 5 mm milling balls can be used.

Ball milling can reduce the diameter of a polycrystalline n-type semiconductor. This may help to prepare a homogeneous and uniform coating of the semiconductor on the sensor platform. In some embodiments, a polycrystalline n-type semiconductor, or a polycrystalline physical mixture of an n-type semiconductor and a p-type semiconductor, can have a diameter, or an average diameter, of about 0.01 µm to about 1 µm, about 0.1 µm to about 1 µm, or about 0.2 µm to about 0.5 µm, or any diameter in a range bounded by, or between, any of these values.

In some embodiments, the length of time for ball milling the material can be between about 0.5 hours to about 1 week, 1 hour to about 72 hours, about 12 hours to about 36 hours. In some embodiments, the above described lengths of time can be for in conjunction with the size of the milling balls described above. In some embodiments, ball milling about 2.00 g $WO_3$/0.05% B, 15.00 ml of methanol, 20 g of 3 mm milling balls and 4 g of 5 mm milling balls can be for about 17 hours.

In some embodiments, the ball milling instrument can be a planetary ball miller. An example of a suitable ball miller can be a SFM-1 Desk top Planetary Ball Miller (MTI Corp, Richmond, Calif., USA). In some embodiments, the planetary ball miller can be set to rotate at about 500 rpm, 1000 rpm to about 2500 rpm, 5000 rpm, or 10000 rpm, or any combination of the above rotating speeds. In some embodiments, the planetary ball miller can rotate at about 1500 rpm.

In some embodiments, the SSA can be increased by sonicating a dispersion of the combustion synthesized material and then selectively removing the reduced size sonicated material. In some embodiments, the sonicating can be by vibrating the sample at about 35 kHz. In some embodiments, the sonicating can be for about 5 minutes to about 6 hours. A suitable sonicator can be a SYMPHONY™ ultrasonic cleaner (VWR, model no. 97043-958). In some embodiments, the sonicating at about 35 kHz can be for about 60 minutes. In some embodiments, selectively removing the reduced size sonicated sample can be by removing aliquots from just below the surface of the sonicated sample dispersion for drop deposition onto the sensor substrate.

In some embodiments, the sensor can detect an analyte. In some embodiments, the analyte can be polar. In some embodiments, the analyte can have a dipole moment of, for example, greater than about 1.00 D, about 1.25 D, about 1.30 D, about 1.40 D, about 1.50 D, about 1.60 D, about 1.70 D, about 1.85 D, about 1.90 D, about 2.00 D, about 2.25 D, or about 2.50 D. Exemplary materials and their dipole moments are described in Table 3 below:

TABLE 3

| Compound | Dipole moment |
| --- | --- |
| Acetone | 2.88 D |
| Ethanol | 1.69 D |
| Methanol | 1.70 D |
| NO | 0.159 D |
| $NO_2$ | 0.316 D |
| $NH_3$ | 1.47 D |
| CO | 0.112 D |
| Ethane | 0 |

TABLE 3-continued

| Compound | Dipole moment |
| --- | --- |
| Isoprene | 0.25 D |
| Isopentane | 0.105 D |

In some embodiments, the analyte can be a gas. In some embodiments, the analyte can be acetone In some embodiments, the analyte can also be ethanol.

In some embodiments, a method for making sensor composition is described, the method comprising creating a n-type semiconductor precursor aqueous solution; heating the solution in a preheated appliance, wherein the preheated appliance has been preheated to substantially near the combustion temperature of the aqueous solution; combustion-reacting the precursor solution; and annealing the combustion reaction product. In some embodiments, the appliance can be preheated to at least about 420° C.

FIG. 1 depicts an embodiment of a sensor element 10. In some embodiments, the sensor element 10 can comprise a first electrode 14 and a second electrode 18. In some embodiments, the sensor can comprise a n-type semiconductor material 16 disposed between the first and second electrodes. In some embodiments, the n-type semiconductor material can be electrically connecting the first and second electrodes. In some embodiments, the n-type semiconductor material can be disposed between and/or physically contacting both the first and second electrodes.

As shown in FIG. 1, the sensor element 10 can comprise a first electrode 14. In some embodiments, the first electrode can comprise one or more electrode fingers 14A, 14B, 14C, 14D, 14E, disposed over a substrate, e.g., alumina support. In some embodiments, the sensor element 10 can also comprise a second electrode 18. In some embodiments, the second electrode 18 can also comprise one or more electrode fingers 18A, 18B, 18C, 18D and 18E. In some embodiments, the respective electrode fingers are interdigitated. In some embodiments, the electrode fingers are sufficiently close to enable closing an electrical circuit across the gap through the semiconducting material. In some embodiments, the electrode fingers can be at least 2, at least 3, at least 4, or at least 5 interdigitated fingers. In some embodiments, there can be a distance between the first electrode 14 and the second electrode 18. In some embodiments, the distance between the electrodes can be between 0.01 mils to about 100 mils, between about 0.1 mils to about 25 mils, and/or between about 0.5 mils to about 10 mils, In some embodiments, an electrode of the device can comprise a plurality of interdigitated fingers, e.g., 14A-14E.

Figure 2:
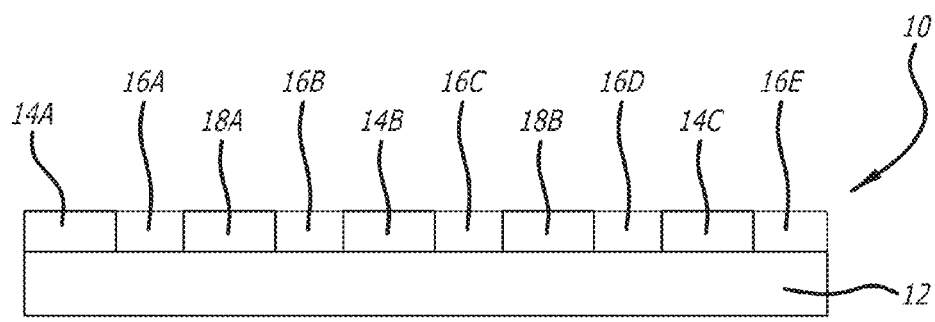
FIG. 2 is an elevational view of an embodiment of a device described herein.

In some embodiments, the sensor element comprises a semiconductor material 16. In some embodiments, the semiconductor material is of a sufficient height to substantially cover the first and second electrodes, In some embodiments, the height of the semiconductor material can be between about 1 µm to about 10 µm, about 2 µm to about 7 µm, about 3 µm to about 5 µm, and or any combination of the above recited values. As shown in FIG. 2, in some embodiments, the semiconductor 16, e.g., 16A, 16B, 16C, 16D, 16E can be disposed between, around, and/or in electrical contact with the first electrode, e.g., electrode fingers 14A, 14B, and 14C, and second electrode, e.g., second electrode fingers 18A and 18B.

Figure 3:
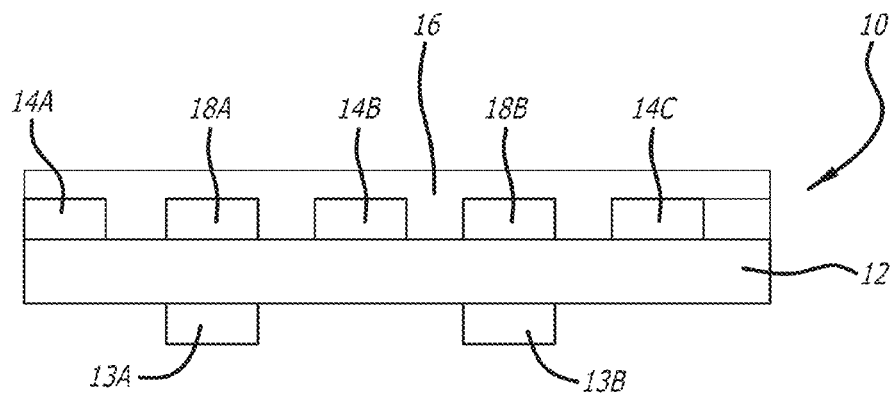
FIG. 3 is an elevational view of an embodiment of a device described herein.

As shown in FIG. 3, in some embodiments the semiconductor can be disposed over the electrodes. In some embodiments, a heater element 13 (e.g., 13A, 13B) can be disposed proximal to the electrodes 14 and 18. Providing a current through the heater element, e.g., a loop or circuit, can heat the substrate and or first and second electrodes to a desired temperature. In some embodiments, the sensor element comprises at least a semiconductor 16 disposed between the electrodes. In some embodiments, the height of the semiconductor material 16 is greater than the height of the electrodes 14 and/or 18. In some embodiments, the semiconductor material comprises primary particles that have a largest dimension less than the length of the gap between the electrode fingers. In some embodiments, the semiconductor 16 comprises semiconductor material having particles with a median diameter of about 0.2 µm to about 1.1 µm, and/or about 0.3 µm to about 1.0 µm. In one embodiment, the median diameter can be between about 0.4 to about 0.8 µm and/or any combination of the described limitation. In some embodiments, the particle median diameter can be about 0.4 µm to about 0.5 µm, e.g., about 0.50086 µm The first and second electrodes can be formed from a conductive material. In some embodiments, the electrodes can be gold (Au), platinum (Pt), palladium (Pd), and/or any mixtures thereof.

In some embodiments, the semiconductor 16 can comprise any of the described doped, loaded and/or physical mixed semiconductors.

The temperature at which the sensor element functions can be affected by different semiconductor materials, dopants, loadants and/or co-catalysts. In some embodiments, the electrodes 14 and 18 are disposed on a substrate 12. In some embodiments, heater element 13 is disposed proximal to the electrodes 14 and 18. In some embodiments, the n-type semiconductor composition combined with any dopants and/or co-catalysts can be formed into a slurry. The slurry can be drop coated on the electrodes and substrate. In some embodiments, the excess slurry can be removed from the acetone sensor element, so that the remaining n-type semiconductor slurry fills the gap between the electrodes, as in FIG. 2.

In some embodiments, the sensor element can detect the presence of an analyte gas within a range of temperatures. In some embodiments, the sensor element can detect the presence of an analyte gas between 0° C. and 400° C. In some embodiments, the sensor element can detect the presence of analyte gases between about 0° C. and about 200° C., about 100° C. and about 300° C., or about 200° C. and about 400° C. In some embodiments, the sensor element can detect the presence of an analyte gas between about 0° C. and about 20° C., about 20° C. and about 40° C., about 40° C. and about 60° C., about 60° C. and about 80° C., about 80° C. and about 100° C., about 100° C. and about 120° C., about 120° C. and about 140° C., about 140° C. and about 160° C., about 160° C. and about 180° C., about 180° C. and about 200° C., about 200° C. and about 220° C., about 220° C. and about 240° C., about 240° C. and about 260° C., about 260° C. and about 280° C., about 280° C. and about 300° C., about 300° C. and about 320° C., about 320° C. and about 340° C., about 340° C. and about 360° C., about 360° C. and about 380° C., or about 380° C. about 400° C., or any temperature bounded by, or between, any of these values. In some embodiments, the sensor can detect the presence of analyte gases at some or any combination of the above described temperatures. In some embodiments, the sensor element can detect the presence of analyte gases at room temperature. In some embodiments, the analyte gas can be acetone, ethanol and/or both acetone and ethanol.

In some embodiments, a polycrystalline n-type semiconductor element, such as a boron doped epsilon $WO_3$, may operate at a temperature above about 150° C. or above about 190° C., such as, about 150° C. to about 400° C., or about 190° C. to about 360° C. In some embodiments, a polycrystalline n-type semiconductor element, such as a boron doped epsilon $WO_3$, may be more sensitive to isoprene than to acetone or ethanol, when operated at a temperature greater than about 280° C. or about 310° C., such as about 280° C., or about 310° C. to about 360° C. In some embodiments, a polycrystalline n-type semiconductor element, such as a boron doped epsilon $WO_3$, may be more sensitive to acetone than to isoprene or ethanol, when operated at a temperature below about 240° C., such as about 180° C. to about 240° C.

In some embodiments, the sensor element can detect the presence of analyte gases in presence of visible light. In some embodiments, the visible light can have a peak wavelength of between about 350 nm, about 375 nm, about 400 nm to about 500 nm, 550 nm, 600 nm, and/or 650 nm, or a range of any combination of the aforedescribed wavelengths. In some embodiments, the sensor element can detect the presence of analyte gases in presence of light having a wavelength of less than 650 nm, less than 600 nm, less than 550 nm, less than 500 nm, less than 450 nm, less than 400 nm. In some embodiments, the sensor element can detect the presence of analyte gases in presence of an LED emitting at about the above described wavelengths, e.g., a blue LED (BLED), e.g., about 455 nm, of power about 30-40 mW/cm$^2$ power. In some embodiments, the sensor can detect the presence of analyte gases at room temperature in the presence of the above described visible light. It is believed that resistivity may decrease at a higher temperature sensor operation when exposed to acetone. In some instances, it appeared that room temperature operation of a sensor could exhibit increased changes in resistivity upon exposure to acetone under BLED light.

In some embodiments, a polycrystalline n-type semiconductor material, such as a gamma phase $WO_3$ having a co-catalyst, e.g. $CeO_2$ or $TiO_2$, may detect volatile organic compounds, such as acetone, ethanol or isoprene, at a low temperature, such as about 10° C. to about 50° C., about 10° C. to about 40° C., about 20° C. to about 30° C., about 25° C. to about 30° C., or about room temperature, when the polycrystalline n-type semiconductor material is exposed to visible light, such as blue light, e.g. light having a wavelength of about 450 nm to 495 nm.

Figure 4A:
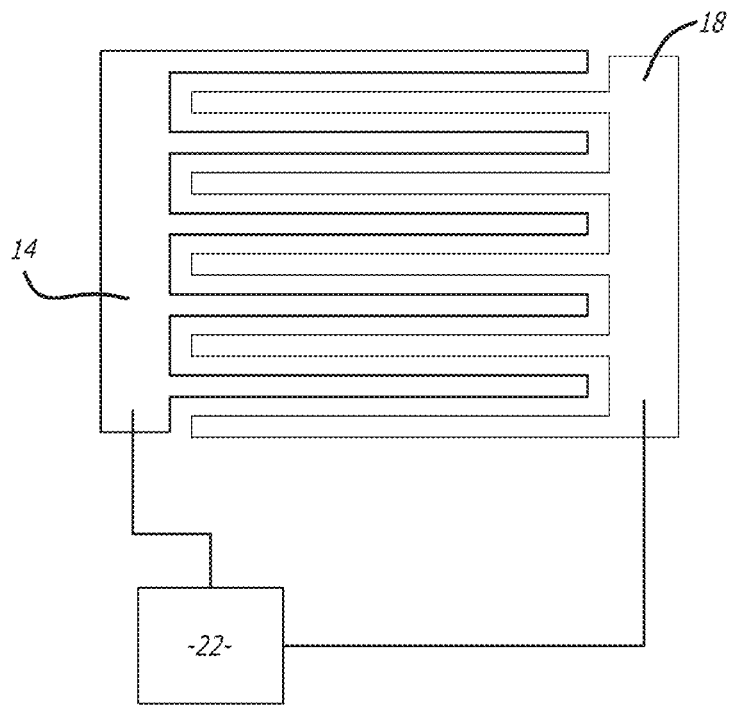
FIG. 4A is a schematic of some embodiments of a device described herein.

FIG. 4A depicts an embodiment of a sensor system 10. In some embodiments, the first electrode 14 and second electrode 18 of sensor element 10 are electrically connected to a resistivity monitor 22. It is believed that the presence of the analyte, e.g., acetone, in close proximity to the electrodes and/or semiconductor may increase the resistance of the circuit between the electrodes 14 and 18, providing a change in the measured resistivity of the circuit. In some embodiments, a measurable correlation between the amount of analyte, e.g., acetone, present in close proximity to the electrodes and the variation in resistance exhibited by the circuit can be effected. In some embodiments, the change in resistivity can be at least about 152 megaohm per 100 part per million (ppm) of analyte present in the tested sampling. The reading is obtained by measuring absolute resistance value and its change directly using computer controlled multimeter.

Figure 4B:
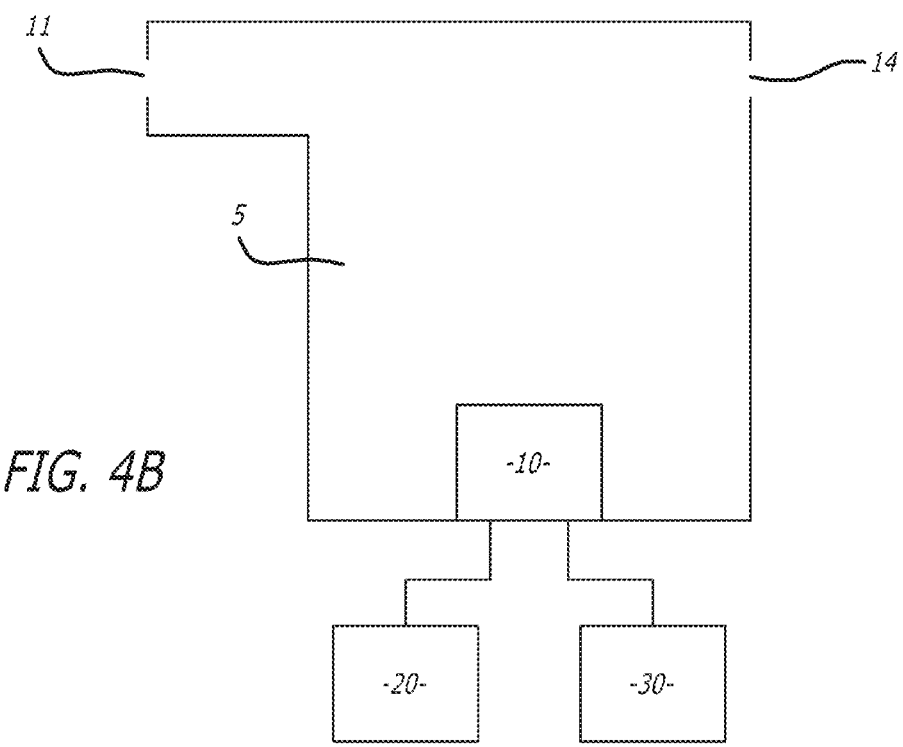
FIG. 4B is a schematic of some embodiments of a device described herein.

FIG. 4B depicts another embodiment of an sensor system 10 for detecting the presence of analyte gases, e.g., acetone, in a volume of gas. The device may comprise a chamber 5 for containing the volume of gas to be evaluated, and a sensor element 10, disposed therein. In some embodiments, the chamber 5 can comprise a gas inlet 11 for allowing inflow of a gas 9. In some embodiments, the chamber 5 can comprise a gas outlet 13 allowing outflow of gas. In some embodiments, the device can comprise a power supply 20, and a measurement device 30 for analyzing the data received from the acetone sensor element.

Figure 7:
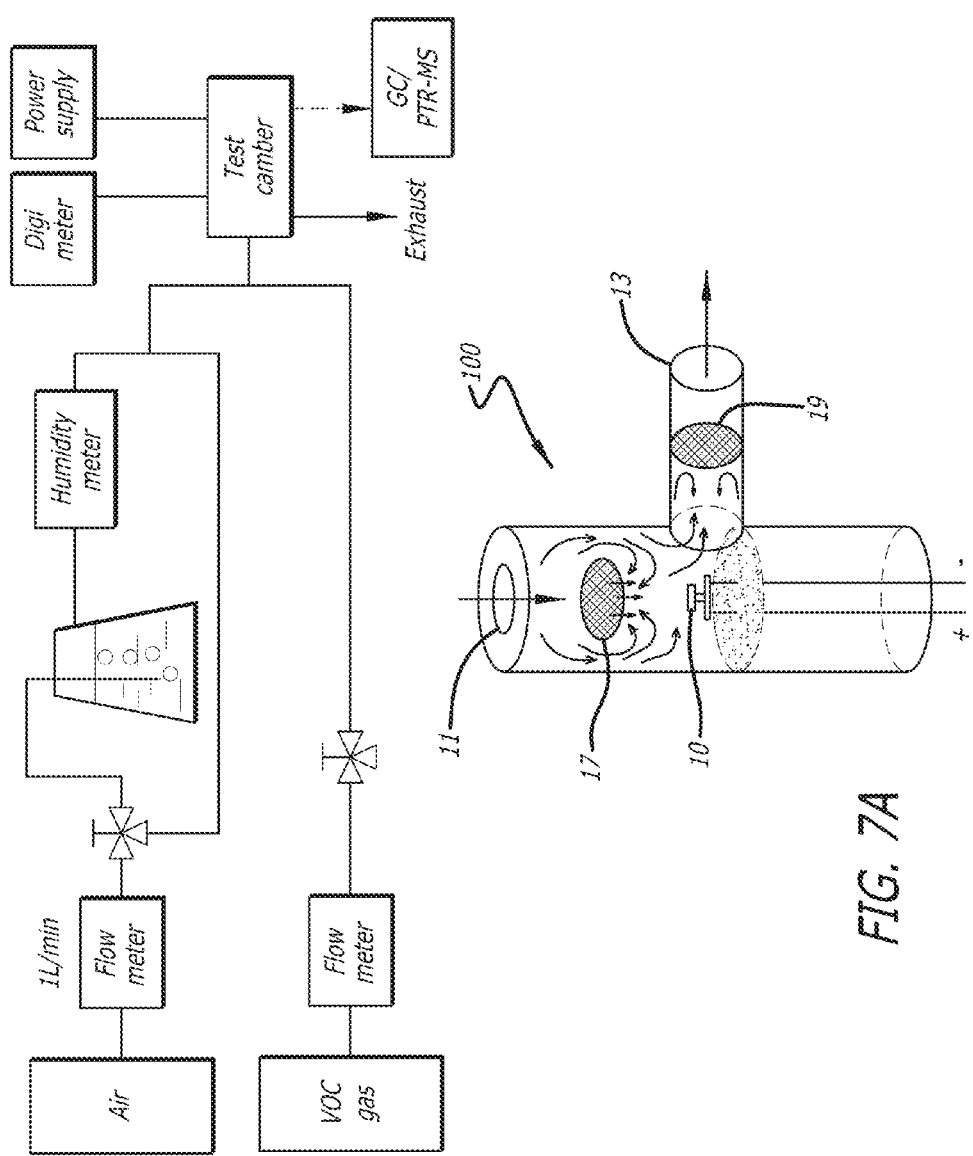
FIG. 7 is a schematic of the testing apparatus used herein.

FIG. 7 depicts a schematic of the acetone sensor system for detecting the presence of acetone in a volume gas as described in Example 11.

FIG. 7A depicts another embodiment of the sensor system 100 for detecting the presence of analyte gases. The apparatus comprises a chamber 17 for retaining a gas sample, a sensor device 10 for analyzing the gas sample, and an airflow disrupting element 17 for affecting the airflow near the sensor device 10. The apparatus may also comprise a gas inlet 11 for introducing a gas sample into the chamber. In some embodiments, the gas inlet 11, a first airflow disrupting element 17, and the sensor device 10, can be arranged co-axially so as to substantially reduce the amount of gas sample that travels from the gas inlet 11 to the sensor device 10 un-impinged. The sensor device can be a solid state sensor for detecting the presence of volatile organic compounds (VOCs) in the gas sample. In some embodiments, the apparatus 100 can comprise a gas outlet 13. In some embodiments, the gas outlet 13 can be disposed such that the gas sample flowing from the gas inlet 11 to the sensor device 10 must change direction of flow before flowing out of the gas outlet 13. In some embodiments, as shown in FIG. 7A, the gas inlet 11, first airflow disrupting element 17, and sensor device 10 can be co-axial, and the gas outlet 13, and second airflow disrupting element 19 disposed therein, can be disposed in the wall of the chamber, oriented perpendicular (90°) to the axis of the aforementioned components. The gas inlet 11 can be in fluid communication with the sensor device 10, the airflow disrupting element 17, and the gas outlet 13. The gas outlet 13 can be in fluid communication with the gas inlet 11, the sensor device 10, the airflow disrupting element 17.

Embodiments also include a method for manufacturing an acetone sensor element as described. In some embodiments, the method comprises the steps of creating a n-type semiconductor precursor aqueous solution, heating the solution in a preheated appliance, wherein the preheated appliance has been preheated to substantially near the combustion temperature of the aqueous solution, combustion-reacting the precursor solution, and annealing the combustion reaction product.

Embodiments also include a method for determining acetone in a mammal's breath comprising exposing a mammalian breath sample to a sensor comprising a polycrystalline n-type semiconductor material of the formula wherein B is boron and $0.0001 < x$ is 0.10, the semiconductor material having an absorption edge of 600 nm or less; and measuring the change in resistivity across the sensor to determine the presence of acetone.

Embodiments also include a method for making sensor element comprising combustion synthesizing a boron doped epsilon or gamma phase $WO_3$ semiconductor; providing an interdigitated sensor element having a first and a second spaced apart electrodes; and disposing said combustion synthesized boron doped epsilon or gamma phase semiconductor between a first and second separated electrodes. In some embodiments, the method can comprise increasing the SSA of the combustion synthesized semiconductor materials. In some embodiments, increasing the SSA can be effected by ball milling the combustion synthesized semiconductor materials. In some embodiments, the SAA can be effected by sonicating a dispersion of the combustion synthesized material and then selectively removing the reduced size sonicated material. In some embodiments, the boron doped epsilon or gamma phase $WO_3$ semiconductor can be ball milled a time and/or manner sufficient to effect the aforedescribed median size description. In some embodiments the method further comprises reducing the semiconductor size population to the aforedescribed ranges, e.g., a median size of about 0.4 to about 0.6 μm. In some embodiments, the aforementioned ranges are achieved by ball milling the boron doped epsilon or gamma phase $WO_3$ semiconductor between about 1 to about 72 hours, e.g., about 17 hours. In some embodiments, the aforementioned ranges are achieved by ball milling the boron doped epsilon or gamma phase $WO_3$ semiconductor between about 500 rpm to about 5000 rpm, e.g., about 1500 RPM. In some embodiments, the aforementioned ranges are achieved by ball milling the boron doped epsilon or gamma phase $WO_3$ semiconductor between about 500 rpm to about 5000 rpm, about 1500 RPM for between about 5 to about 25 hours, e.g., about 17 hours. In some embodiments the method further comprises adding a first ball size population to the boron doped epsilon or gamma phase $WO_3$ semiconductor. In some embodiments, the ball used in ball milling can be $Al_2O_3$, and/or $ZrO_2$. In some embodiments, the $ZrO_2$ balls can comprise plural size populations. In some embodiments, the plural size populations can comprise a first population of about 3 mm $ZrO_2$ and a second population of about 5 mm $ZrO_2$.

It has been discovered that embodiments described herein have improved operational environmental parameters and/or sensitivity to acetone as compared to other sensors embodiments. These benefits are further shown by the following examples, which are intended to be illustrative of the embodiments of the disclosure, but are not intended to limit the scope or underlying principles in any way.

EXAMPLES

Sensor Materials Development and Characterizations:

Example 1. Making Boron Doped Epsilon Phase $WO_3$

Figure 5:
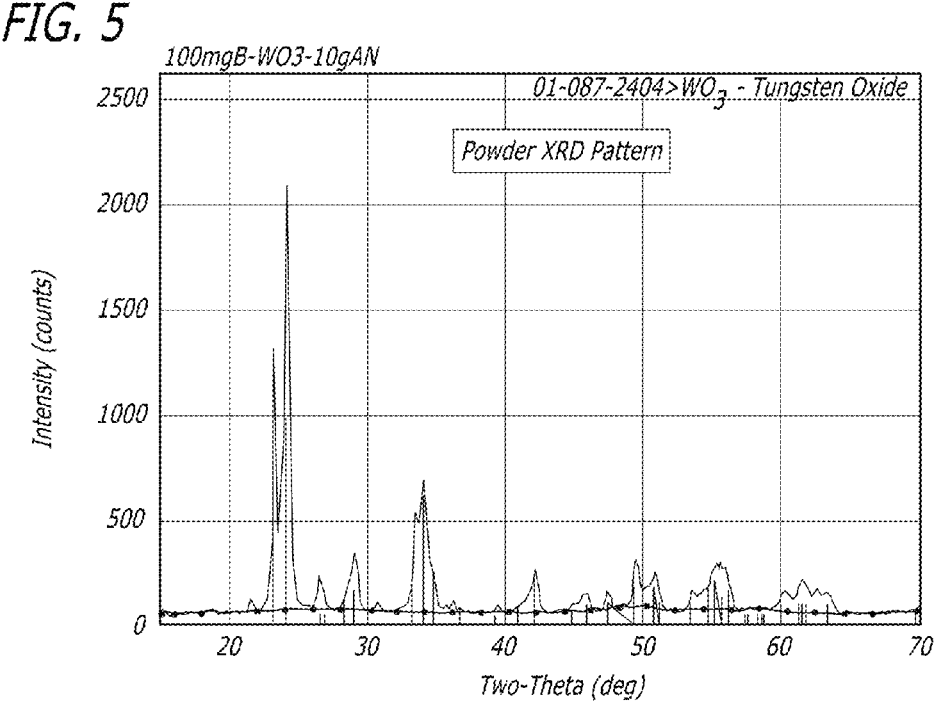
FIG. 5 depicts X-ray diffraction patterns of an embodiment of an n-type material described herein.
Figure 12A:
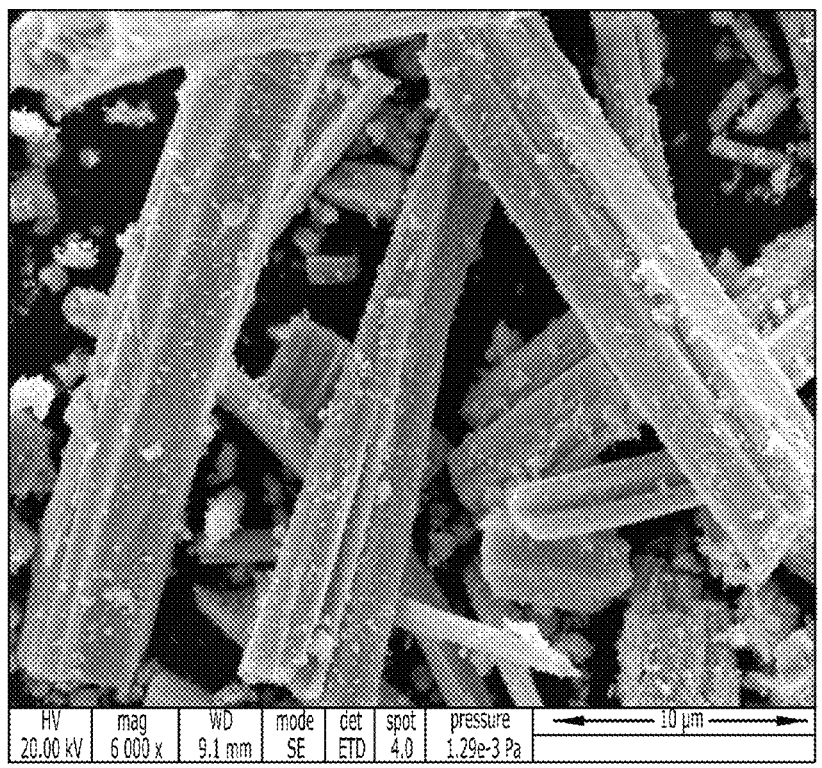
FIG. 12A is a scanning electron microscope image of combustion synthesized particles as described in Example 1.

Ammonium meta tungstate hydrate (5 g), boric acid (100 mg), carbohydrazide (fuel) (2 g) and ammonium nitrate (oxidizer) (10 g) were dissolved in 50 ml of deionized (DI) water. The aqueous solution was then placed in a muffle furnace, which had been preheated to about 420° C., and then heated for about 20 min or until combustion of the materials was substantially completed. After the combustion of the sample material was completed, the product was annealed in air at about 420° C. for an additional about 20 min. The body color of the powder appeared orange-yellow and boron doped $WO_3$ was confirmed by comparison with powder XRD pattern (FIG. 5) with a standard epsilon $WO_3$ x-ray diffraction (TOFF PDF card number 01-087-2404). A scanning electron micrograph of the resultant material is shown in FIG. 12A.

Three 0.05 g samples of B doped $WO_3$ particles were analyzed by ICP-MS to determine the content of various elements. Each sample was mixed with 1 mL nitric acid and 3 mL hydrochloric acid, then heated at about 110° C. for about 1 hour. After cooling, a sufficient amount of an internal standard solution (e.g., with B and/or B doped $WO_3$) was added to dilute the dissolved sample solution to about a 100 g sample aliquot for ICP-MS analysis. The sample aliquot was then spiked with known concentrations of Sc and In. Common standard elements, blanks, and the sample solution were then introduced to an Agilent 7500cx Inductively Coupled Plasma-Mass Spectrometer (ICP-MP). The concentrations of the approximately the respective elements in the sample solutions were quantitatively determined and shown in Table 3A below.

TABLE 3A

| Sample (0.19 wt % B WO$_3$) | % Epsilon WO$_3$ (XRD) | Wt % Ratio of Boron (ICP-MS) |
|---|---|---|
| Sample 1 | 74.7 | 0.11 |
| Sample 2 | 72.5 | 0.084 |
| Sample 3 | 72.1 | 0.082 |

Examples 2-10

Examples 2-10 were made in a manner similar to example 1, except that the amounts of boric acid ("B"), carbohydrazide ("C") and/or ammonium nitrate ("D") were varied as described in Table 4 below.

TABLE 4

| Example | Precursors | Combustion Temperature | Annealing Temperature | Nominal Composition |
|---|---|---|---|---|
| 1 | A = 5 g; B = 100 mg; C = 10 g; D = 2 g | 420° C. | 420° C./20 min | 0.378 wt % ratio B in WO$_3$ |
| 2 | A = 5 g; B = 1.322 g; C = 10 g; D = 2 g | 420° C. | 420° C./20 min | 5 wt % ratio B in WO$_3$ |
| 3 | A = 5 g; B = 1.322 g; C = 5 g; D = 2 g | 420° C. | 420° C./20 min | 5 wt % ratio B in WO$_3$ |
| 4 | A = 5 g; B = 1.322 g; C = 5 g; D = 1 g | 420° C. | 420° C./20 min | 5 wt % ratio B in WO$_3$ |
| 5 | A = 5 g; B = 0.666 g; C = 10 g; D = 2 g | 420° C. | 420° C./20 min | 2.5 wt % ratio B in WO$_3$ |
| 6 | A = 5 g; B = 0.333 g; C = 10 g; D = 2 g | 420° C. | 420° C./20 min | 1.5 wt % ratio B in WO$_3$ |
| 7 | A = 5 g; B = 0.05 g; C = 10 g; D = 2 g | 420° C. | 420° C./20 min | 0.225 wt % ratio B in WO$_3$ |
| 8 | A = 5 g; B = 0.200 g; C = 10 g; D = 2 g | 420° C. | 420° C./20 min | 0.90 wt % ratio B in WO$_3$ |
| 9 | A = 5 g; B = 0 mg; C = 10 g; D = 2 g | 420° C. | 420° C./20 min | 0 wt. % ratio B in WO$_3$ (gamma-WO$_3$) |
| 10 | A = 5 g; B = 0 mg; C = 10 g; D = 2 g | 420° C. | 420° C./20 min | 0 wt. % ratio B in WO$_3$ (gamma-WO$_3$) |

A is ammonium meta tungstate hydrate (source for W behaves as fuel)
B is boric acid (dopant)
C is ammonium nitrate (oxidizer)
D is carbohydrazide (fuel)

Examples 11-13

Example 11. Noble Metal Loading of Boron Doped Epsilon WO$_3$ 1 g of the Example 1, made in the manner described above, and 17.12 mg of [Pt(NH$_3$)4](NO$_3$)$_2$ were placed in 10 mL distilled water and stirred, at about 90° C. for about 2 hours in a 40 mL closed vial reactor. The closed vial was then quenched in room temperature tap water and filtered through a membrane filter (0.05 μm pore size), washed with DI water at least 3 times and finally dried at about 110° C. for overnight (about 15 hours), resulting in about 45 mg of 1 wt % Pt loaded epsilon-phase WO$_3$.

Examples 12, 13, and 14 were made in a similar manner to Example 11 (1% Pt-ε-WO$_3$), except that 1 g of gamma phase WO$_3$ (Sigma-Aldrich, St. Louis, Mo., USA) was used instead of epsilon phase WO$_3$ for Example 12 (1% Pt-γ [gamma]-WO3), 1 g of gamma WO$_3$, without boron (B) was used instead of 1% Pt-epsilon-phase WO$_3$ for Example 13 and 13 g of gamma phase WO$_3$ and 8 g of CeO$_2$ in a physical mix, 1 g of this physical mix was used instead of 1 g of 1% Pt-epsilon-phase WO$_3$ in Example 14.

Example 14

Figure 12B:
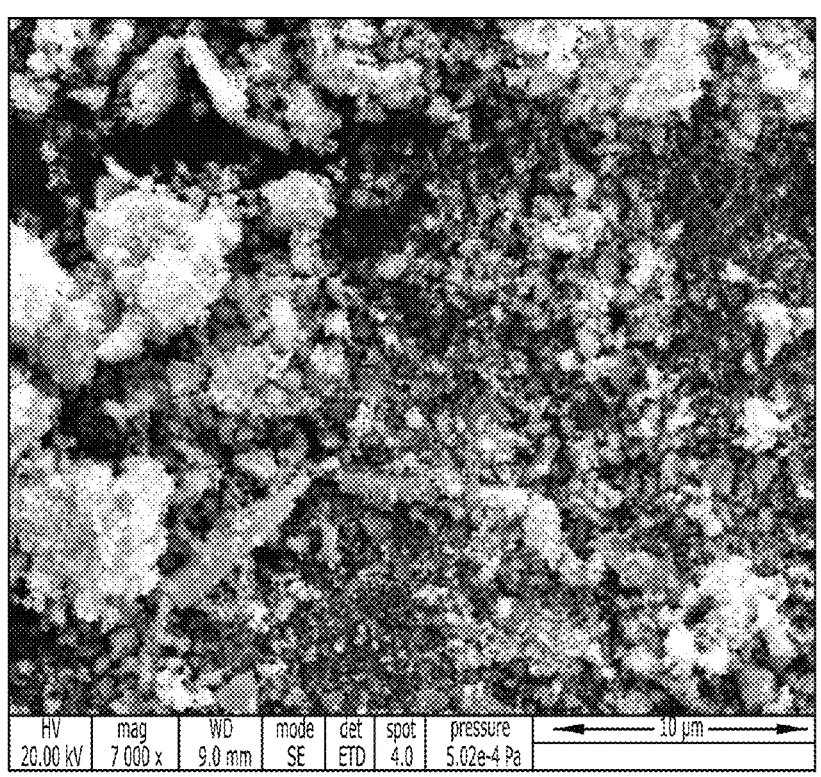
FIG. 12B is a scanning electron microscope image of combustion synthesized particles as described in Example 11.

Example 14A. Ball Milled Slurry 2.00 g WO$_3$/0.05% B made as described above in Example 1 and 15.00 ml of methanol were added to high purity alumina jar for solvent-based slurry preparation, and the contents in the mill jar were then stirred by hand until the mixture seemed liquid-like. 20 g of ZrO$_2$ milling media of 3 mm diameter and 4 g of ZrO$_2$ milling media of 5 mm diameter were then added to the alumina jar, and the mixture in the mill jar was milled by bench-top planetary ball mill (MTI Corporation, Richmond Calif.) for about 17 hours at about 1500 rpm at room temperature. The resultant mixture was then dried at about 110° C. for about 2 hours in air. An scanning electron micrograph of the resulting ball milled slurry embodiment is shown of FIG. 12B.

Example 14B

In another example, 2.00 g WO$_3$/0.19 wt % B made as described above was used instead of 2.00 g WO$_3$/0.05% B.

Example 14C. Particle Size Analysis

Particle size distributions of before and after ball milled were attained with a Horiba LA-300 particle size distribution analyzer (Horiba Scientific, Edison, N.J., USA).

2 g of aqueous sodium pyrophosphate decahydrate (SPD) was dissolved in about 2 L of reverse osmosis water (RO H$_2$O) to make the SPD solution (0.1 wt % sodium pyrophosphate decahydrate).

2 L of additional RO H$_2$O were circulated and sonicated in the Horiba LA-300 sample chamber for one minute for cleaning ("De-bubble" on). The just circulated and sonicated RO $H_2O$ was drained from the sample chamber and the chamber refilled with the SPD solution (Horiba settings at Circulation "8" and "De-bubble"). The instrument was blanked (settings at "Init. Alignment", "Alignment", "Blank") and repeated to assure percent total transmission (T %) of the blank was T %=100%.

Xenon lamp at 300 W output power, for about 60 minutes at about 120° C.

Drop coated sensor 2 (SE-2); 3 (SE-3), 4 (SE-4) and 5 (SE-5) were constructed in the same manner as described above, except the material dispersed in the IPA was as indicated in Table 5 below.

TABLE 5

| | | Solution | | Processing | |
|---|---|---|---|---|---|
| | Material | Solvent | Con. | drop coating | Baking |
| SE-2 | 1% Pt—LiZn—$Ti_3O_8$ | IPA | 9 mg/0.4 ml | 10 µL drop × 10 | 1 hr-120° C. under Xeon |
| SE-3 | 1% Pt—γ-$WO_3$ | IPA | 9 mg/0.4 ml | 10 µL drop × 10 | 1 hr-120° C. under Xeon |
| SE-3 | 1% Pt—ε-$WO_3$ | IPA | 9 mg/0.4 ml | 10 µL drop × 10 | 1 hr-120° C. under Xeon |
| SE-4 | γ-$WO_3$ w/o B | IPA | 9 mg/0.4 ml | 10 µL drop × 10 | 1 hr-120° C. under Xeon |
| SE-5 | γ-$WO_3$ w/o B + $CeO_2$ | IPA | 9 mg/0.4 ml | 10 µL drop × 10 | 1 hr-120° C. under Xeon |

An initial amount of about x g of ball milled 0.19 wt % B doped $WO_3$ (made as described in Example 12B above [SE-1 BM]) was transferred into about 25 ml of the SPD solution and mixed well (for about 5 minutes). The SE-1BM mixture was loaded into the sample chamber until the T % dropped to about 75% to 80%. Upon reaching such T %, with settings selected at Circulation "8", sonicating for 10 minutes, "De-bubble" during the sonication for 10 min and "R.R.Index"

Figure 13:
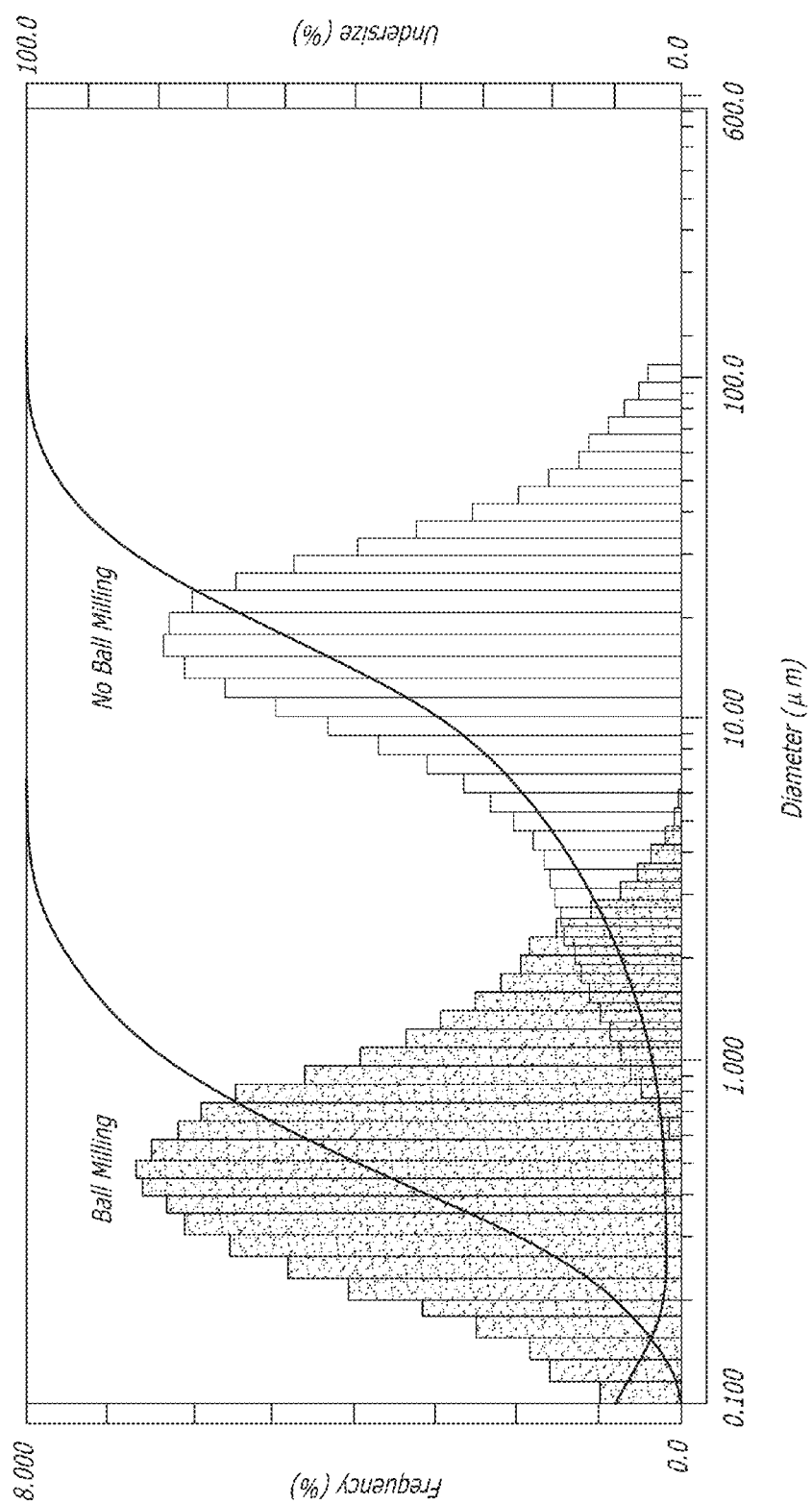
FIG. 13 is a graph depicting the size populations of n-type semiconductor material used in the sensor embodiments as described in Example 14.

(refractive index of the solvent") at about 1.654

$$\left(\frac{R_{powder}}{R_{solvent}} = \frac{\text{Refractive index of the powder}}{\text{Refractive index of the solvent}} = \frac{WO_3}{H_2O} = \frac{2.22}{1.55} = 1.654\right),$$

the particle size distribution was attained (see FIG. 13). The particle size distribution for a non-ball milled sample (SE-3) was prepared in the same manner described above, except that SE-3 material was used instead of ball milled 0.19 wt % B doped $WO_3$ (SE-1BM). The results are depicted in FIG. 13.

The decrease and/or shift in the diameter size of the particles is shown in FIG. 13. The median diameter for the $WO_3$/0.05% B particles without ball milling was about 13.7233 µm while the median diameter for $WO_3$/0.05% B particles with the ball milling as described above was about 0.5086 µm.

Example 15: Sensor Fabrication & Drop Coating of Sensor Material

Example 15A: Without Ball Milling

About 9 mg of platinum loaded ε-phase tungsten oxide as prepared above, was mixed with isopropyl alcohol (IPA) (0.4 ml) and sonicated for 60 minutes. About ten 10 µl aliquots of the dispersion were removed from just below the surface of the sonicated dispersion and then were dropped onto a sensor element (0.1×0.1 inch electrode, $Al_2O_3$ substrate, 10 mils thick, electrode material Au, electrode spacing 1 mils, finger width 4 mils, finger length 0.1 inch and with 3 electrode pairs, P/N 614; Synkera technologies, Colorado, USA), having a surface temperature of about 120° C., and dried between each additional drop. The drop coated sensor (SE-1) was then baked on under a full-spectrum Xenon lamp at 300 W output power, for about 60 minutes at about 120° C.

Figure 6:
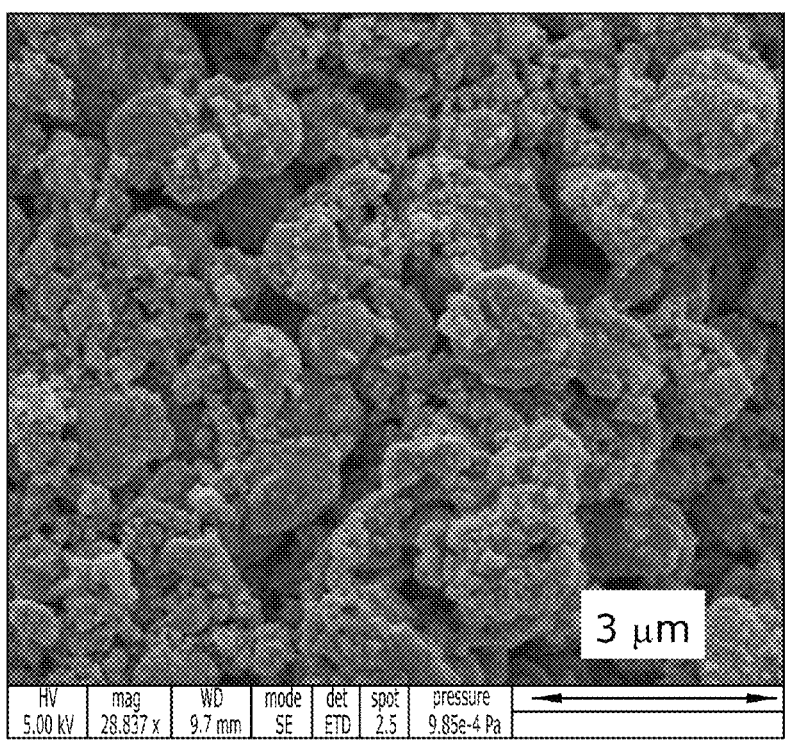
FIG. 6 is a scanning electron microscope image of surfaces comprising the composite element described herein.

An SEM photograph of 1 wt % ratio Pt loaded ε-$WO_3$ (SE-3) is shown in FIG. 6.

Example 15B Sensor Fabrication with Ball Milling

About 10 mg of ball milled tungsten oxide as prepared above, was mixed with methanol (1.0 ml) and sonicated for 60 minutes. About seven 10 µl aliquots of the dispersion were dropped onto a sensor element (0.1×0.1 inch electrode, $Al_2O_3$ substrate, 10 mils thick, electrode material Au, electrode spacing 4 mils, finger width 4 mils, finger length 0.1 inch and with 3 electrode pairs, P/N 614; Synkera technologies), having a surface temperature of about 120° C., and dried between each additional drop. The drop coated sensor (SE-1BM) was then baked on under a full-spectrum Xenon lamp at 300 W output power, for about 60 minutes at about 120° C.

Example 16: Acetone Sensor Evaluation

Figure 9:
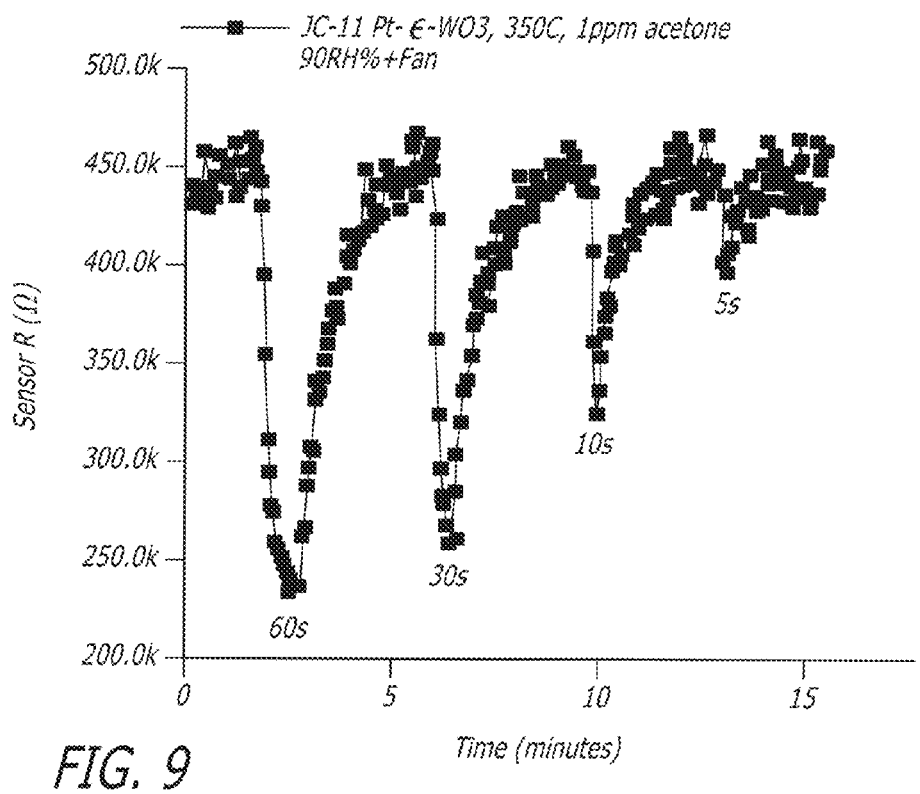
FIG. 9 is a graph depicting the resistivity response to 1 ppm acetone sample of a sensor embodiment as described in Example 13.

The Sensor Element 3 (SE-3) constructed as described in the example above, was placed inside a metal chamber having about 850 mL volume, with the sensor electrodes connected to a multimeter (Tektronix DMM 4050, 6½ Digit Precision Multimeter, Tektronix, Inc., Beaverton, Oreg., USA), set to measure resistivity (ohms) at about 40 mΩ, placed in a completely darkened room under ambient atmospheric conditions. See FIG. 7. The sensor electrodes were then exposed to an operating temperature of about 350° C. Acetone free air (compressed synthetic air [CAS 132259-10-0], Airgas, LLC, San Marcos, Calif., USA) having a relative humidity of about 90%, was released into the container at about 1 ml/minute and bled from the chamber at the same rate (so as to minimize pressurization of the chamber), for about 10 minutes and resistivity baseline readings were recorded. 1 ppm acetone/air gas (A-030-1090-100PNA compressed 1 ppm acetone/synthetic air, Mesa Specialty Gases & Equipment, Long Beach, Calif., USA) was then released into the container for varying amounts of time, e.g., 60 sec, about 30 sec, about 10 sec, about 5 sec, and the resistivity of the sensor element was recorded. The gaseous environment within the chamber was assessed by gas chromatographer attached to mass spectrophotometer (Agilent gas chromatograph, Model 7890A; Agilent mass spectrophotometer, Model 240). The results are shown in FIG. 9. FIG. 9 shows that the sensor element exhibited a sensitivity to about 1 ppm acetone in air while the sensor operating temperature was at about 350° C.

Example 17: Acetone Sensor Evaluation

The Sensor Elements 5 and 4 were constructed as described in Example 16 above was also tested as described immediately above, except that the sensor was maintained at about room temperature and the sensor was exposed to an array of blue light emitting light emitting diodes, the BLED emitting at about 455 nm wavelength, about 35-40 mW/cm$^2$. The results are provided in Table 6:

TABLE 6

| Material | Sensitivity (100 ppm) (w/LED) | Response time (min) | Sensitivity (100 ppm) (wout/LED) | Sensitivity (2 ppm) (w/LED) | Acetone decompose experiment |
|---|---|---|---|---|---|
| γ-WO$_3$-CeO$_2$ | 7.2 | 3.6 | 1.0 | 1.0 | 66% |
| γ-WO$_3$ | 1.0 | N/A | 1.0 | 1.0 | N/A |

Figure 8:
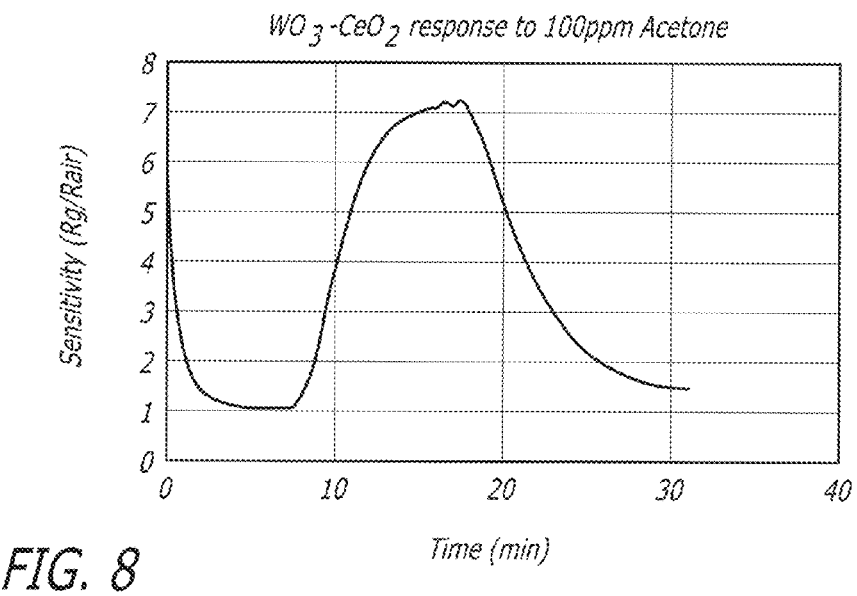
FIG. 8 is a graph depicting the resistivity response to 100 ppm acetone sample of a sensor embodiment as described in Example 14.

FIG. 8 shows that the sensor element exhibited a sensitivity to about 100 ppm acetone in air while the sensor operating temperature was at room temperature.

Example 18: Acetone Sensor Evaluation

The SE-1BM was constructed as described in the example above was also tested in a manner similar to that described above, FIG. 7. In this example, instead of an 850 ml metal chamber as described immediately above, a T-tubed test chamber (TC-1) as described in U.S. Provisional Application 62/064,680, filed 16 Oct. 2014, incorporated by reference herein for all it discloses, was used. TC-1 was built from a 7.62 cm long (polycarbonate) tube with an inner diameter of 2.6 cm. The test chamber had gas outlet, with a 1 cm inner diameter, forming a perpendicular t-junction with the apparatus chamber, the center of the gas outlet was in line with the sensor device. The center of the gas outlet and the sensor device (sensor as in Example 1, constructed on a Syntek 614 chip with a heater circuit) were located 3.81 cm from the end of the apparatus. The apparatus chamber was sealed on the bottom end approximately 4.3 cm from the top, just below the gas outlet aperture. The apparatus had a gas inlet that was 1 cm in circumference in the center of the top end of the apparatus. The apparatus also had a wire mesh screen acting as an airflow reducing element filling the gas outlet tube. The airflow reducing element was a Super-Corrosion-Resistant Type 316 Stainless Steel Wire Cloth Disc, with a wire diameter of 0.01 inches, a mesh size of 40×40, an opening size of 0.015 inches, creating an open area of about 36% (McMaster-Carr 2930T43, McMaster-Carr, Los Angeles, Calif., USA). FIG. 7A shows the above described test chamber. The airflow disrupting element was suspended in the apparatus by four wire tethers to hold the screen in place. The airflow disrupting element was 1.5 cm in diameter, located in the chamber of the apparatus 1 cm above the surface of the sensor device, and concentric with the test chamber tube. The wire mesh screen was a Super-Corrosion-Resistant Type 316 Stainless Steel Wire Cloth Disc (McMaster-Carr 2930T63, McMaster-Carr), with a wire diameter of 0.0045 inches, a mesh size of 100×100, an opening size of 0.0055 inches, creating an open area of about 30%.

Figure 10:
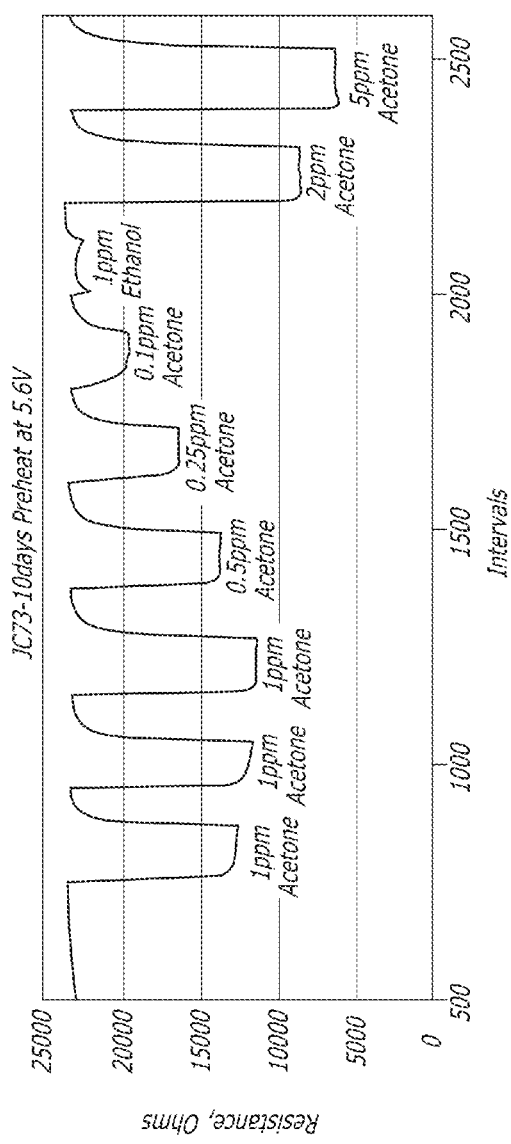
FIG. 10 is a graph depicting the resistivity response to 1 ppm acetone sample of a sensor embodiment as described in Example 15.
Figure 11:
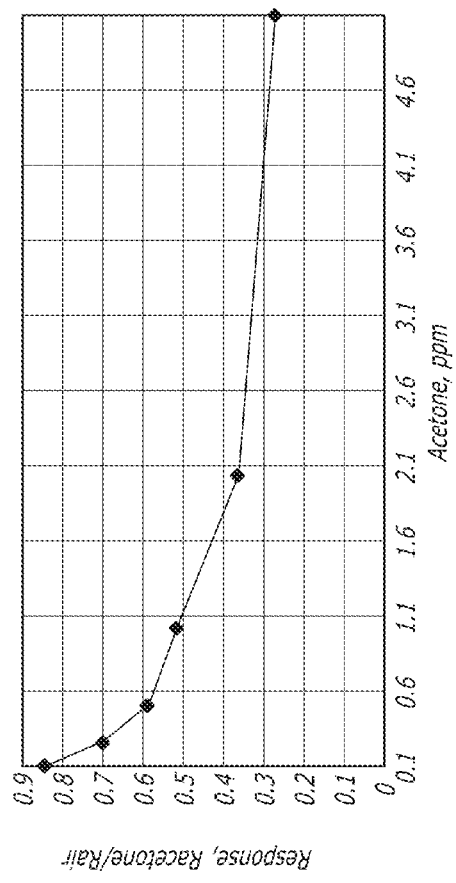
FIG. 11 is a graph depicting the resistivity response to different concentration of acetone sample of a sensor embodiment as described in Example 15.

The Sensor Element 3 (with heater circuit substrate Synkera P/N 614) constructed as described in the example above, was placed inside a T-shaped chamber described above, with the sensor electrodes connected to a multimeter (Tektronix DMM 4050, 6½ Digit Precision Multimeter, Tektronix, Inc.), set to measure resistivity (ohms) at about 40 mΩ, under ambient atmospheric conditions. See FIG. 7. The sensor electrode heater circuit (614) were then exposed to 5.6 volts with a driving current of about 0.156 amps using a power source of Gw Instek PST-3202 to heat the sensor body for about 72 hours. During the measurement a voltage of 5.2 Volts and 0.153 amps to heat the sensor body to about 300° C. Acetone free air (compressed synthetic air [CAS 132259-10-0], Airgas, LLC, San Marcos, Calif., USA) having a relative humidity of about 90%, was released into the container at about 1 ml/minute and bled from the chamber at the same rate (so as to minimize pressurization of the chamber), for about 5 minutes and resistivity baseline readings were recorded. A pulse of about 10 ppm acetone/air gas (A-030-1090-100PNA compressed 1 ppm acetone/synthetic air, Mesa Specialty Gases & Equipment) was then released into the container at about 1 liter/min for about 5 minutes and the resistivity of the sensor element was recorded. An acetone free/synthetic air pulse followed by 1 ppm sample acetone pulse was repeated two times. An acetone free pulses followed by 15 ml, 2.5 ml, 1 ml/min acetone sample pulses with respective intervening acetone free separation pulses were then applied to the sensor system. The results are provided in FIG. 10. The sensor response as a function of acetone concentration extracted from FIG. 10 is shown in FIG. 11.

Example 18A

Figure 15:
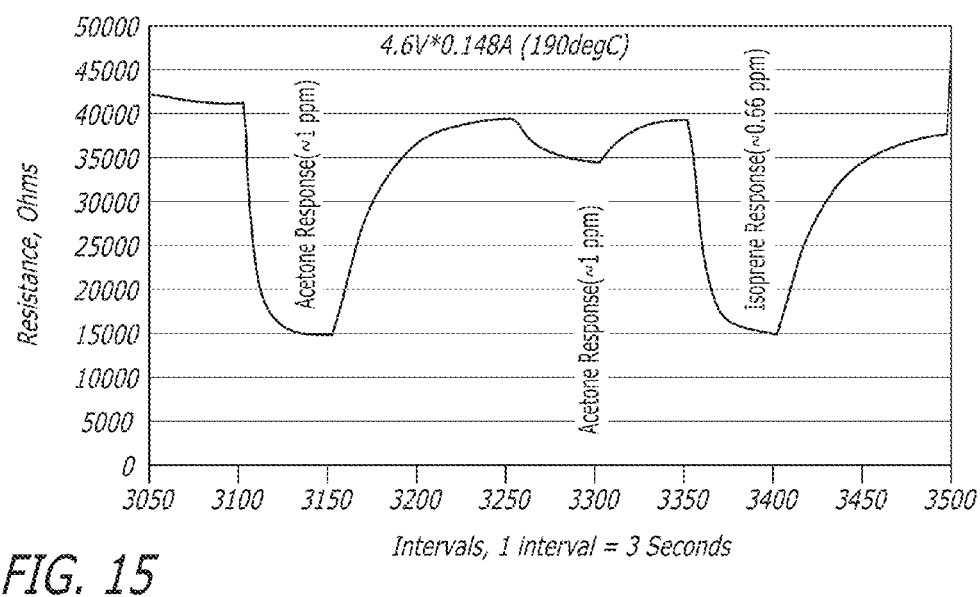
FIG. 15 is a graph depicting the resistivity response to 1 ppm acetone sample, 0.65 ppm ethanol and 0.66 ppm isoprene of a sensor embodiment as described in Example 18A.

Sensor Element 1 (with heater circuit substrate Synkera P/N 614) constructed as described above, was placed inside a T-shaped chamber described above, with the sensor connected to a multimeter (Tektronix DMM 4050, 6½ Digit Precision Multimeter, Tektronix, Inc., Beaverton, Oreg., USA), set to measure resistivity (ohms) at about 40 kΩ, under ambient atmospheric and in dark conditions. The sensor was heated to about 195° C. by applying voltage of 3.8 volts and current of 0.137 amps to platinum resistive heater. Acetone-free air (compressed synthetic air [CAS 132259-10-0], Airgas, LLC, San Marcos, Calif., USA) having a relative humidity of greater 90% was released into the container of T-tube at about 1.5 Liter/min to establish a base of line of resistivity (See first portion of resistivity profile in FIG. 15 wherein there is an apparent plateau in the resistance profile at about 42,000 ohms corresponding with interval 3,050 to about 3,100) of sensor for about 300 seconds. Then, concurrently with the 1.5 L/min air flow, 15.1 ppm acetone/synthetic air mixture was passed at about 110 mL/min of into the system and the resistivity change was monitored at a temperature of 195° C. for about 150 seconds. The acetone flow was then closed to re-establish the base line of resistivity of sensor and flushed with acetone free synthetic air for about 300 seconds (a return of the resistivity from about 15,000 ohms to about 39,000 ohms as seen in FIG. 15 at about interval 3,150 to about 3,250). Ethanol gas (99.4 ppm acetone/synthetic air mixture, flow rate of 10 mL/min) was then mixed with aforementioned 1.5 L/min synthetic air flow to observe the resistivity change at the temperature of 195° C. for about 150 seconds. The ethanol flow was closed again to re-establish the base line of resistivity of sensor and flushed with ethanol free synthetic air for about 300 seconds (a return of the resistivity from about 35,000 ohms to about 39,000 ohms as seen in FIG. 15 at about interval 3,300 to 3,350). Isoprene gas (100.9 ppm isoprene/synthetic air mixture, flow rate of 10 mL/min) was then mixed with isoprene free synthetic air (1.5 L/min) to observe the resistivity change at the temperature of 195° C. for about 150 seconds.

Isoprene flow was then closed again to stabilize the base line of resistivity of sensor (a return of the resistivity from about 15,000 ohms to about 37,500, at about interval 3,500).

Examples 19-27

Examples 19 to Example 27 were tested in a similar manner to that described in Example 18A above, except that the sensor device was heated to varying temperatures by applying varying voltages and currents as set forth in Table 7 below.

TABLE 7

| Example | Sensor temperature (° C.) | Voltage applied (volts) | Current applied (amps) |
|---|---|---|---|
| Example 18A | 195 | 3.8 | 0.137 |
| Example 19 | 215 | 4.0 | 0.141 |
| Example 20 | 225 | 4.2 | 0.143 |
| Example 21 | 240 | 4.4 | 0.145 |
| Example 22 | 260 | 4.6 | 0.148 |
| Example 23 | 275 | 4.8 | 0.151 |
| Example 24 | 290 | 5.0 | 0.153 |
| Example 25 | 310 | 5.2 | 0.156 |
| Example 26 | 320 | 5.4 | 0.158 |
| Example 27 | 340 | 5.6 | 0.160 |

Figure 14:
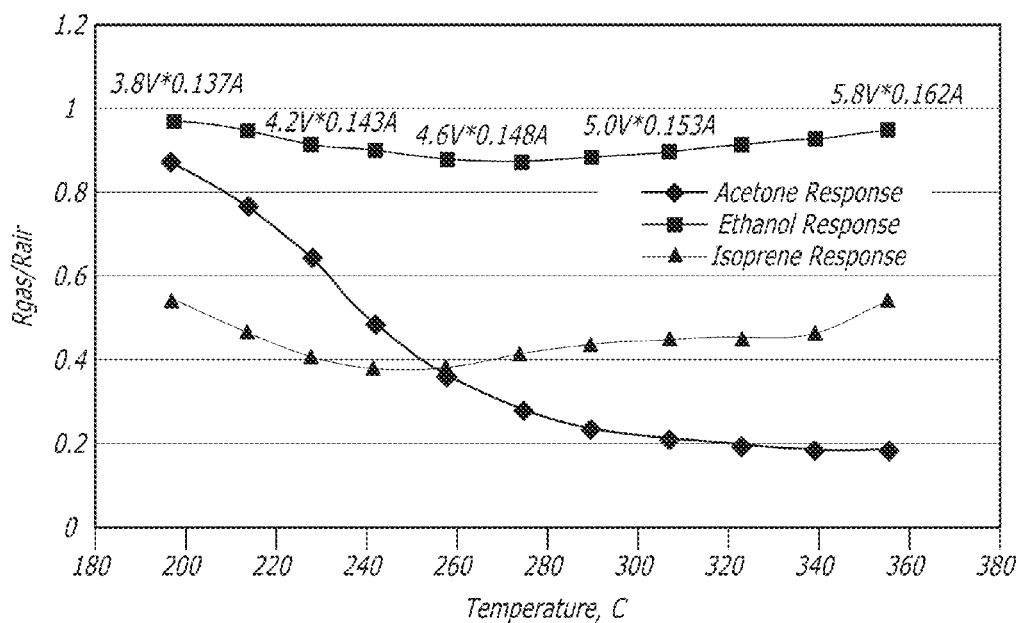
FIG. 14 is a graph depicting the size populations of n-type semiconductor material used in the sensor embodiments as described in Example 14

FIG. 14 shows that the sensor element exhibited a relatively constant sensitivity for ethanol and isoprene, while exhibiting a higher sensitivity (higher Rair/Rgas) for acetone at higher temperatures, e.g., 300° C. or greater as compared with 200° C.

EMBODIMENTS

The following embodiments are contemplated:

Embodiment 1

A gas sensor element comprising:
a first electrode and second electrode, wherein the first electrode and the second electrode are separated by a gap of about 1 to about 10 mils; and
a polycrystalline n-type semiconductor material wherein the semiconductor material physically contacts both the first and second electrodes.

Embodiment 2

The gas sensor of any embodiment herein, such as embodiment 1, wherein the polycrystalline n-type semiconductor is represented by the formula $P_{1-x}B$, wherein P is an n-type semiconductor material; B is boron and x is greater than about 0.0001 and not greater than about 0.10.

Embodiment 3

The gas sensor of any relevant embodiment herein, such as embodiment 1 or 2, wherein the semiconductor material has an absorption edge of 600 nm or less.

Embodiment 4

The gas sensor element of any relevant embodiment herein, such as embodiment 1, 2, or 3, wherein the polycrystalline n-type semiconductor material comprises epsilon phase $WO_3$.

Embodiment 5

The gas sensor element of any relevant embodiment herein, such as embodiment 4, wherein the epsilon phase $WO_3$ is doped with boron.

Embodiment 6

The gas sensor element of any relevant embodiment herein, such as embodiment 5, wherein the boron is present at about 0.001% to about 1% by weight of the polycrystalline n-type semiconductor.

Embodiment 7

The gas sensor element of any relevant embodiment herein, such as embodiment 1, 2, 3, 4, 5, or 6, wherein the polycrystalline n-type semiconductor material is combustion synthesized.

Embodiment 8

The gas sensor element of any relevant embodiment herein, such as embodiment 1, 2, 3, 4, 5, 6, or 7, wherein the polycrystalline n-type semiconductor is at a temperature of about 190° C. to about 360° C.

Embodiment 9

The gas sensor element of any relevant embodiment herein, such as embodiment 1, 2, 3, 4, 5, 6, 7, or 8, wherein the polycrystalline n-type semiconductor material comprises gamma phase $WO_3$.

Embodiment 10

The gas sensor element of any relevant embodiment herein, such as embodiment 1, 2, 3, 4, 5, 6, 7, 8, or 9, further comprising a co-catalyst.

Embodiment 11

The gas sensor element of any relevant embodiment herein, such as embodiment 10, wherein the co-catalyst is a noble metal.

Embodiment 12

The gas sensor element of any relevant embodiment herein, such as embodiment 12, wherein the noble metal is palladium, gold, platinum or iridium.

Embodiment 13

The gas sensor element of any relevant embodiment herein, such as embodiment 10, wherein the co-catalyst is $CeO_2$ or $TiO_2$.

Embodiment 14

The gas sensor element of any relevant embodiment herein, such as embodiment 13, wherein the co-catalyst is $CeO_2$.

Embodiment 15

The gas sensor element of any relevant embodiment herein, such as embodiment 1, 2, 3, 4, 5, 6, 7, 8, 9, 10, 11, 12, 13, or 14, wherein the polycrystalline n-type semiconductor material is exposed to blue light.

Embodiment 16

The gas sensor element of any relevant embodiment herein, such as embodiment 1, 2, 3, 4, 5, 6, 7, 8, 9, 10, 11, 12, 13, 14, or 15, wherein the polycrystalline n-type semiconductor material is at a temperature of about 10° C. to about 40° C.

Embodiment 17

The gas sensor element of any relevant embodiment herein, such as embodiment 10, 11, 12, 13, 14, 15, or 16, wherein the ratio of semiconductor material to co-catalyst is about 40-60 molar % semiconductor material to about 60-40% co-catalyst.

Embodiment 18

The gas sensor element of any relevant embodiment herein, such as embodiment 10, 15, 16, or 17, wherein the co-catalyst is a transition metal oxide (p-type).

Embodiment 19

The gas sensor element of any relevant embodiment herein, such as embodiment 18, wherein the transition metal oxide is a Co, Mn, Ni, or Cu oxide (p-type).

Embodiment 20

The gas sensor element of any relevant embodiment herein, such as embodiment 1, 2, 3, 4, 5, 6, 7, 8, 9, 10, 11, 12, 13, 14, 15, 16, 17, 18, or 19, wherein the polycrystalline n-type semiconductor material is ball milled.

Embodiment 21

A method for determining acetone in a subject's breath comprising exposing a mammalian breath sample to a gas sensor comprising a gas sensor element of any relevant embodiment herein, such as embodiment 1, 2, 3, 4, 5, 6, 7, 8, 9, 10, 11, 12, 13, 14, 15, 16, 17, 18, 19, or 20, wherein the presence of acetone is detected by a change in resistivity across the sensor.

Embodiment 22

The method of any relevant embodiment herein, such as embodiment 21, wherein the gas sensor operates at about 10° C. to about 50° C. and the gas sensor element is exposed to blue light.

Embodiment 23

The method of any relevant embodiment herein, such as embodiment 21, wherein the gas sensor operating temperature is about 190° C. to about 360° C.

Embodiment 24

The method of any relevant embodiment herein, such as embodiment 21 or 23, wherein the sensor is not exposed to blue light.

Embodiment 25

The method of any relevant embodiment herein, such as embodiment 23 or 24, wherein the gas sensor is operated from about 280° C. to about 360° C., and the gas sensor is more sensitive to isoprene than to acetone.

Embodiment 26

The method of any relevant embodiment herein, such as embodiment 21 or 23, wherein the gas sensor is operated from about 180° C. to about 240° C., and the gas sensor is more sensitive to acetone than to isoprene.

Embodiment 27

A method for making a sensor element comprising: combustion synthesizing a boron doped epsilon or gamma phase $WO_3$ semiconductor; providing an interdigitated sensor element having a first and second spaced apart electrodes; and disposing said combustion synthesized boron doped epsilon or gamma phase semiconductor between a first and second separated electrodes.

Embodiment 28

The method of any relevant embodiment herein, such as embodiment 27, further comprising increasing the synthesized boron doped epsilon or gamma phase semiconductor specific surface area to greater than 10 $m^2/g$ by ball milling the boron doped epsilon or gamma phase $WO_3$ semiconductor between about 5 to about 25 hours.

Embodiment 29

The method of any relevant embodiment herein, such as embodiment 27 or 28, wherein increasing the Brunauer-Emmett-Teller (BET) of the boron doped epsilon or gamma phase $WO_3$ semiconductor comprises ball milling the boron doped epsilon or gamma phase $WO_3$ semiconductor between about 1 hour to about 72 hours.

Embodiment 30

The method of any relevant embodiment herein, such as embodiment 27, 28, or 29, wherein increasing the BET of the boron doped epsilon or gamma phase $WO_3$ semiconductor comprises sonicating the boron doped epsilon or gamma phase $WO_3$ semiconductor before disposition between the first and second electrode.

Embodiment 31

The method of any relevant embodiment herein, such as embodiment 27, 28, 29, or 30, further comprising adding a metal oxide to the boron doped epsilon or gamma phase $WO_3$ semiconductor.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing embodiments herein (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the disclosed embodiments and does not pose a limitation on the scope of any claim. No language in the specification should be construed as indicating any non-claimed element essential to the practice of the disclosed embodiments.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventor for carrying out the spirit of the present disclosure. Of course, variations on these described embodiments will become apparent to those of ordinary skill in the art upon reading the foregoing description. The inventor expects skilled artisans to employ such variations as appropriate, and the inventor intends for the disclosed embodiments to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed:

1. A gas sensor element comprising:
   a first electrode and second electrode, wherein the first electrode and the second electrode are separated by a gap of about 1 to about 10 mils; and
   a polycrystalline n-type semiconductor material comprising:
   epsilon phase $WO_3$ that is doped with boron;
   wherein the polycrystalline n-type semiconductor material physically contacts both the first and second electrodes.

2. The gas sensor element of claim 1, wherein the boron is present at about 0.001% to about 1% by weight of the polycrystalline n-type semiconductor material.

3. The gas sensor element of claim 1, wherein the polycrystalline n-type semiconductor material is combustion synthesized.

4. The gas sensor element of claim 1, wherein the polycrystalline n-type semiconductor is at a temperature of about 190° C. to about 360° C.

5. The gas sensor element of claim 1, further comprising a noble metal mixed with the polycrystalline n-type semiconductor material.

6. The gas sensor element of claim 5, wherein the noble metal is palladium, gold, platinum, or iridium.

7. The gas sensor element of claim 1, wherein the polycrystalline n-type semiconductor material is exposed to blue light.

8. The gas sensor element of claim 1, wherein the polycrystalline n-type semiconductor material is at a temperature of about 10° C. to about 40° C.

9. The gas sensor element of claim 1, wherein the polycrystalline n-type semiconductor material is ball milled.

10. The gas sensor element of claim 1, wherein the semiconductor material has an absorption edge of 600 nm or less.

11. The gas sensor element of claim 1, further comprising a co-catalyst.

12. The gas sensor element of claim 11, wherein the co-catalyst is $CeO_2$ or $TiO_2$.

13. The gas sensor element of claim 11, wherein the co-catalyst is $CeO_2$.

14. The gas sensor element of claim 11, wherein the co-catalyst is a transition metal oxide (p-type).

15. The gas sensor element of claim 14, wherein the transition metal oxide is a Co, Mn, Ni, or Cu oxide (p-type).

* * * * *